US011291822B2

(12) United States Patent
Jones et al.

(10) Patent No.: US 11,291,822 B2
(45) Date of Patent: *Apr. 5, 2022

(54) BREAKAWAY MEDICAL TUBING CONNECTOR

(71) Applicant: Site Saver, Inc., Fayetteville, AR (US)

(72) Inventors: Spencer A. Jones, Fayetteville, AR (US); Jordan Mykleby, Fayetteville, AR (US); Vance Clement, Fayetteville, AR (US)

(73) Assignee: Site Saver, Inc., Fayetteville, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/122,481

(22) Filed: Dec. 15, 2020

(65) Prior Publication Data
US 2021/0236794 A1 Aug. 5, 2021

Related U.S. Application Data

(60) Continuation of application No. 16/272,559, filed on Feb. 11, 2019, now Pat. No. 10,864,362, which is a
(Continued)

(51) Int. Cl.
*A61M 39/10* (2006.01)
*A61M 5/168* (2006.01)
(Continued)

(52) U.S. Cl.
CPC ...... *A61M 39/105* (2013.01); *A61M 5/16813* (2013.01); *A61M 39/10* (2013.01);
(Continued)

(58) Field of Classification Search
CPC ............... A61M 39/105; A61M 39/20; A61M 39/1011; A61M 39/10; A61M 39/26;
(Continued)

(56) References Cited

U.S. PATENT DOCUMENTS 5,320,390 A * 6/1994 Kodama ............. F16L 37/0985
285/308
5,775,671 A * 7/1998 Cote, Sr. ............... A61M 39/26
251/149.8
(Continued)

FOREIGN PATENT DOCUMENTS

EP 2736584 B1 1/2013
JP 2017209149 11/2017
(Continued)

OTHER PUBLICATIONS

European Search Report, dated Sep. 21, 2021, 12 pages.
Abstract of JP2017209149, one page.

*Primary Examiner* — Patrick C Williams
(74) *Attorney, Agent, or Firm* — Waller Lansden Dortch & Davis, LLP; Matthew C. Cox

(57) ABSTRACT

A breakaway medical tubing connector and method for joining two sections of medical tubing includes a pump side member and a patient side member positioned axially opposite from the pump side member. The patient side member has a first channel disposed within the pump side member and a first valve disposed within the first channel. The pump side member has a second channel disposed within the patient side member and a second valve disposed within the second channel. The first valve may be an active valve and the second valve may be a passive valve. A securing bar may be disposed on the pump side member and a securing arm may be disposed on the patient side member for providing a detachable coupling of the two members.

6 Claims, 26 Drawing Sheets

Related U.S. Application Data division of application No. 15/875,494, filed on Jan. 19, 2018, now abandoned, which is a continuation-in-part of application No. 15/237,607, filed on Aug. 15, 2016, now Pat. No. 10,655,768.

(60) Provisional application No. 62/204,845, filed on Aug. 13, 2015.

(51) Int. Cl.
| | |
|---|---|
| *F16L 37/32* | (2006.01) |
| *A61M 39/24* | (2006.01) |
| *A61M 39/26* | (2006.01) |
| *F16L 37/098* | (2006.01) |
| *A61M 39/20* | (2006.01) |

(52) U.S. Cl.
CPC ........ *A61M 39/1011* (2013.01); *A61M 39/20* (2013.01); *A61M 39/24* (2013.01); *A61M 39/26* (2013.01); *F16L 37/098* (2013.01); *F16L 37/32* (2013.01); *A61M 2039/1027* (2013.01); *A61M 2039/1061* (2013.01); *A61M 2039/1066* (2013.01); *A61M 2039/242* (2013.01); *A61M 2039/2406* (2013.01); *A61M 2039/2426* (2013.01)

(58) Field of Classification Search
CPC .............. A61M 39/24; A61M 5/16813; A61M 2039/2406; A61M 2039/242; A61M 2039/1066; A61M 2039/1061; A61M 2039/1027; A61M 2039/2426; F16L 37/098; F16L 37/32

See application file for complete search history.

(56) References Cited

U.S. PATENT DOCUMENTS

| | | | |
|---|---|---|---|
| 5,820,614 A | 10/1998 | Erskine et al. | |
| 7,766,039 B2* | 8/2010 | Zuck | F16L 37/127 137/614.04 |
| 7,955,317 B2* | 6/2011 | Fournie | A61M 39/26 604/533 |
| 2006/0129109 A1 | 6/2006 | Shaw et al. | |
| 2009/0200796 A1 | 8/2009 | Lai | |
| 2010/0286596 A1 | 11/2010 | Hofmann et al. | |
| 2017/0067586 A1 | 3/2017 | Jones et al. | |

FOREIGN PATENT DOCUMENTS

| | | | |
|---|---|---|---|
| WO | 2013016623 | A2 | 1/2013 |
| WO | 2013016623 | A3 | 1/2013 |

* cited by examiner

BREAKAWAY MEDICAL TUBING CONNECTOR

CROSS-REFERENCE TO RELATED APPLICATIONS

This application is a continuation of U.S. patent application Ser. No. 16/272,559 filed Feb. 11, 2019 entitled BREAKAWAY MEDICAL TUBING CONNECTOR, which is a divisional of U.S. patent application Ser. No. 15/875,494 filed Jan. 19, 2018 entitled BREAKAWAY MEDICAL TUBING CONNECTOR, which is a continuation in part of U.S. patent application Ser. No. 15/237,607 filed Aug. 15, 2016 entitled BREAKAWAY CONNECTOR, which claims priority to U.S. Provisional Patent Application Ser. No. 62/204,845, and which are herein incorporated by reference in their entireties.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND

The present disclosure relates generally to connectors for intravenous medical tubing. More particularly, the present disclosure relates to automatically sealing breakaway intravenous line connectors.

The use of medical tubing for transferring fluids to and from a patient is common practice in a medical setting. Intravenous technologies and techniques have advanced to a degree such that many devices associated with intravenous applications are discreet and often forgotten by a patient. As such, it is not uncommon for a patient to attempt a movement that is limited by the medical tubing and the devices connected at each end of the medical tubing. This often results in discomfort, pain, and even danger to a patient as the access point into a vein of the patient is damaged. This can cause deep abrasions, tearing, and even hemorrhaging. This is especially dangerous to the patient if the access point is a major vein, artery, or organ.

When an access point is compromised by an accidental movement, it can result in an unsanitary and dangerous environment as the patient can hemorrhage and the fluids that were either collected or being introduced into the patient will pour out from the storage containers. A patient may panic and attempt to reestablish the connection which can be dangerous as there is a risk of line contamination, which can result in extreme danger to the patient, and the patient is not trained to accomplish this task. The line, insertion point, and fluids may have been contaminated in the detachment and if the patient is able to reestablish the line, the patient is potentially introducing pathogens and other contaminates directly into the body. This can result in serious and deadly infections as well as other serious complications.

What is needed then are improvements in devices and methods for preventing accidental removal of intravenous insertion sites and breakaway connectors for medical tubing.

BRIEF SUMMARY

This Brief Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

One aspect of the disclosure is a breakaway connector device for placement between two medical tubing apparatuses. Commonly in current medical practice, there is a device or tube inserted within the patient that, upon exit from the patient's body, presents an apparatus for the connection of an external piece of tubing. The secondary container of fluid for infusion, or a container for removal of fluid, sometimes with a pumping mechanism along the tubing in-between the container and the patient. The connection point between these respective medical tubing segments is of utmost importance, as it presents an entry point for pathogens and is usually very close to the patient and therefore near the insertion site.

The present disclosure allows a sealed, fluid connection between the two connecting pieces of the medical tubing, but allows a disengagement of the tubing sections from one another once a specific tension threshold or threshold range is applied, before the adhesive or securement devices fail, ultimately preventing the adverse event of premature device removal. The two ends of the devices remain attached to their respective sides of the tubing serve as protective barriers to external pathogens, and also occludes the flow of fluids to serve as a barrier to fluid leakage out of the patient or ultimately from the containers. The devices are only attachable with a special tool which is able to access the mechanism for attachment within the device.

Numerous other objects, advantages and features of the present disclosure will be readily apparent to those of skill in the art upon a review of the following drawings and description of a preferred embodiment.

DETAILED DESCRIPTION

Figure 1:
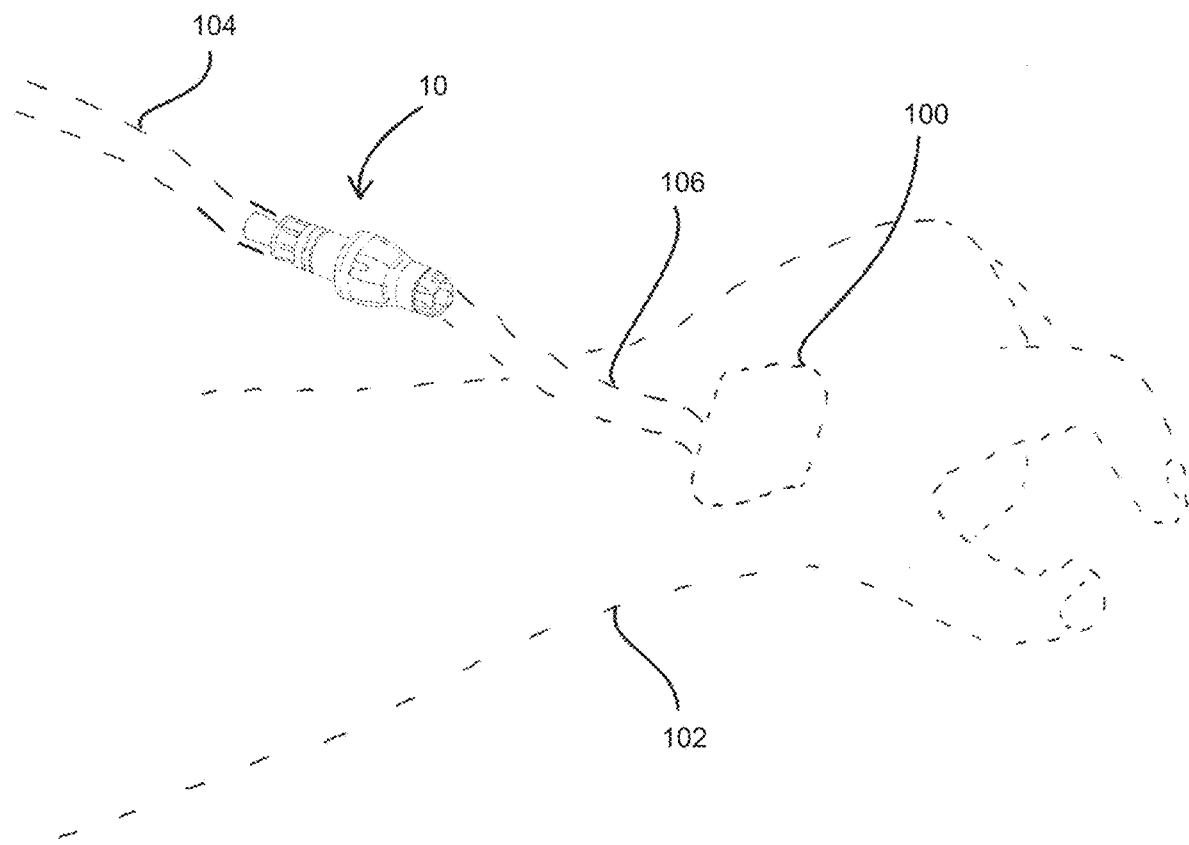
FIG. 1 is a view of an embodiment of an exemplary apparatus in use.

While the making and using of various embodiments of the present invention are discussed in detail below, it should be appreciated that the present invention provides many applicable inventive concepts that are embodied in a wide variety of specific contexts. The specific embodiments discussed herein are merely illustrative of specific ways to make and use the invention and do not delimit the scope of the invention. Those of ordinary skill in the art will recognize numerous equivalents to the specific apparatus and methods described herein. Such equivalents are considered to be within the scope of this invention and are covered by the claims.

In the drawings, not all reference numbers are included in each drawing, for the sake of clarity. In addition, positional terms such as "upper," "lower," "side," "top," "bottom," etc. refer to the apparatus when in the orientation shown in the drawing, or as otherwise described. A person of skill in the art will recognize that the apparatus can assume different orientations when in use.

Figure 2:
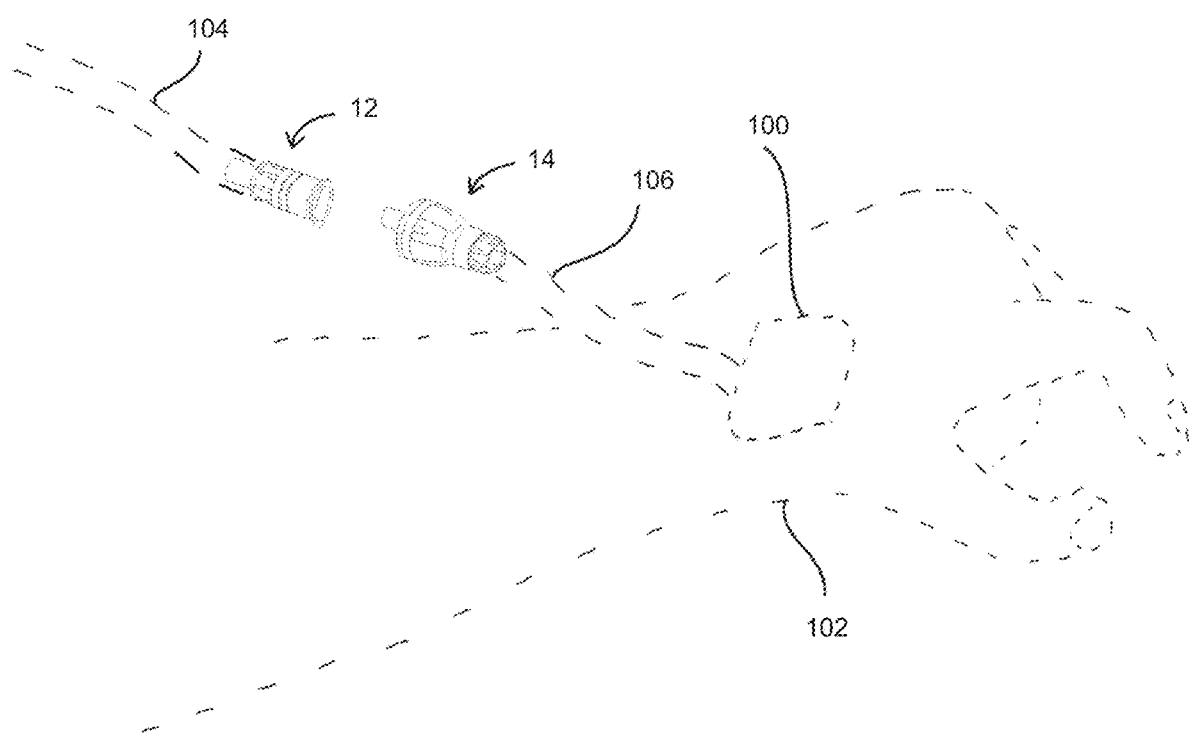
FIG. 2 is a view of an embodiment of an exemplary apparatus after separation while in use.

Referring further to the drawings, FIG. 1 illustrates an exemplary application of a patient safety disconnect, or a breakaway medical tubing connector apparatus (apparatus) 10, positioned on a medical tube line. Apparatus 10 may be used in any appropriate medical gas, fluid, or solid delivery, extraction, or monitoring line, such as an intravenous (IV) line. Apparatus 10 in some embodiments includes a pump side member 12 and a patient side member 14. Apparatus 10 is configured to decouple such that the pump side member 12 and the patient side member 14 separate if a threshold amount of tensile force is applied in opposing axial directions along the apparatus 10. As seen in FIG. 1, a delivery site 100 such as a catheter or other intravenous needle device is located on a patient 102. A first line 104 extends between apparatus 10 and a source or sink for fluid, gas, or solid material moving through the line. The first line 104 has a free end coupled to the apparatus 10. A second line 106 extends between apparatus 10 and a delivery site 100. The second line 106 is coupled at a free end to the apparatus 10. When the pump side member 12 and the patient side member 14 are coupled, one or more valves within the apparatus 10 are opened to allow fluid, gas, and/or solid to travel through the apparatus 10 between the first line 104 and the second line 106. In the event the patient 102 moves in a manner to impart a threshold tensile force on the first and second lines 104, 106, apparatus 10 may separate such that the pump side member 12 becomes disengaged from the patient side member 14, as shown in FIG. 2. One or more valves in apparatus 10 may close upon disengagement of pump side and patient side members 12, 14 such that flow of fluid, gas, or solid is prevented from exiting each of the pump side and patient side members 12, 14.

In some embodiments, apparatus 10 is designed such that the level of tensile force required to cause the pump side and patient side members 12, 14 to disengage is sufficiently low to provide disengagement of apparatus 10 prior to unintentional removal of delivery site 100 from patient 102.

Figure 3:
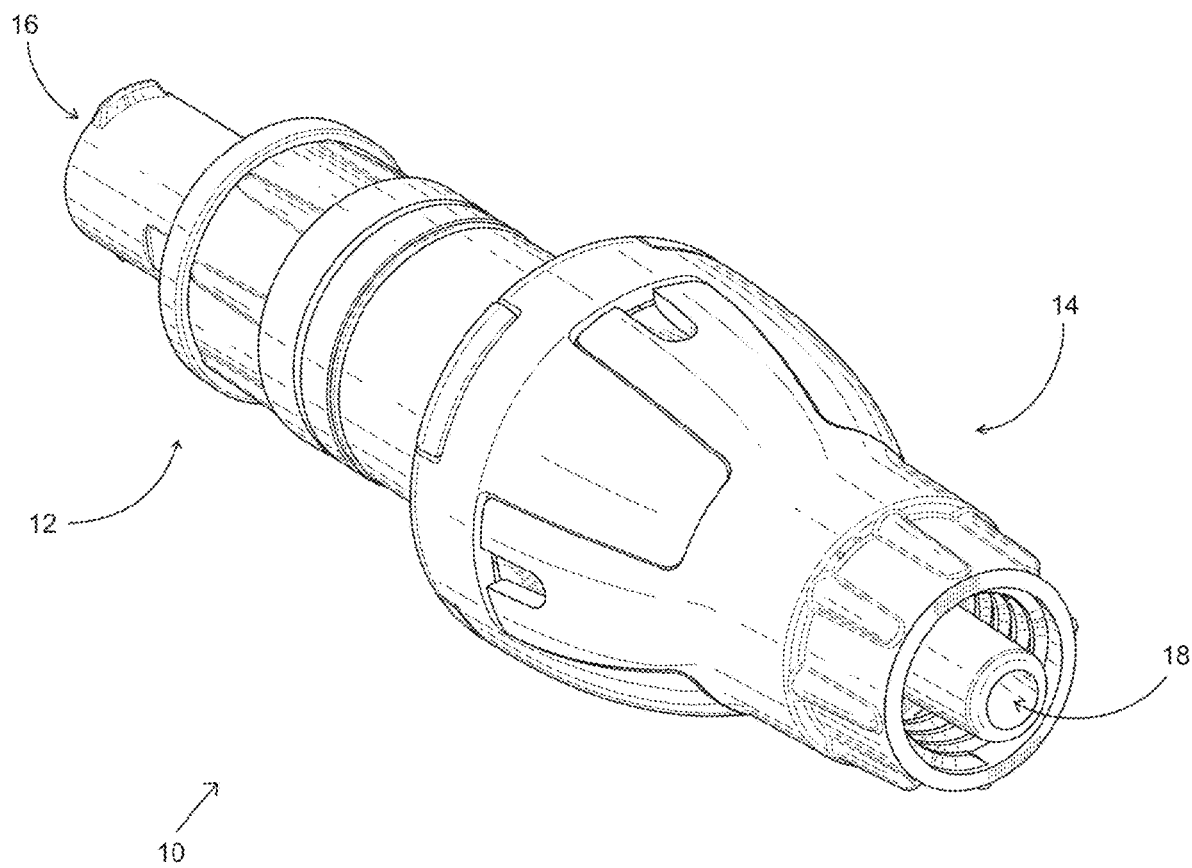
FIG. 3 is a perspective view of an embodiment of an exemplary apparatus.

Referring to FIG. 3, in some embodiments apparatus 10 includes a pump side member 12 and a patient side member 14 positioned axially opposite the pump side member 12. The pump side member 12 includes a first fitting 13 in some embodiments. The first fitting 13 can include any suitable tube or hose fitting configured to engage a corresponding free end of a medical tube. For example, in some embodiments, first fitting 13 can include a hose barb fitting, a female luer fitting, a male luer fitting, a male threaded fitting, a female threaded fitting, or any other suitable fitting. Similarly, the patient side member 14 includes a second fitting 15 in some embodiments. The second fitting 15 can be any suitable tube or hose fitting configured to engage a corresponding free end of a medical tube. For example, in some embodiments, second fitting 15 can include a hose barb fitting, a female luer fitting, a male luer fitting, a male threaded fitting, a female threaded fitting, or any other suitable fitting.

Although many forms, embodiments, and implementations are possible, this particular embodiment as shown in FIG. 3 will be discussed in detail while other embodiments will be described in this application, including combining subparts into a single part and variations to a specific implementation of the apparatus. The apparatus 10 may be inserted onto an existing medical line. One end may be specifically adapted to directly couple to a medical line. Other embodiments may provide alternative connections to the medical line such as luer locks and other similar adaptors. One end of the apparatus 10 may be preinstalled on a portion of a medical line. This allows for a second medical line, typically a patient end of the medical line with the delivery site 100 into the patient 102, to be directly coupled to the patient side member 14 of the apparatus 10 via an adaptor, luer lock, or quick disconnect coupling. However, the apparatus 10 may be configured to couple to many existing lines as these lines often are currently configured with a luer lock on the end of the medical line.

Figure 4:
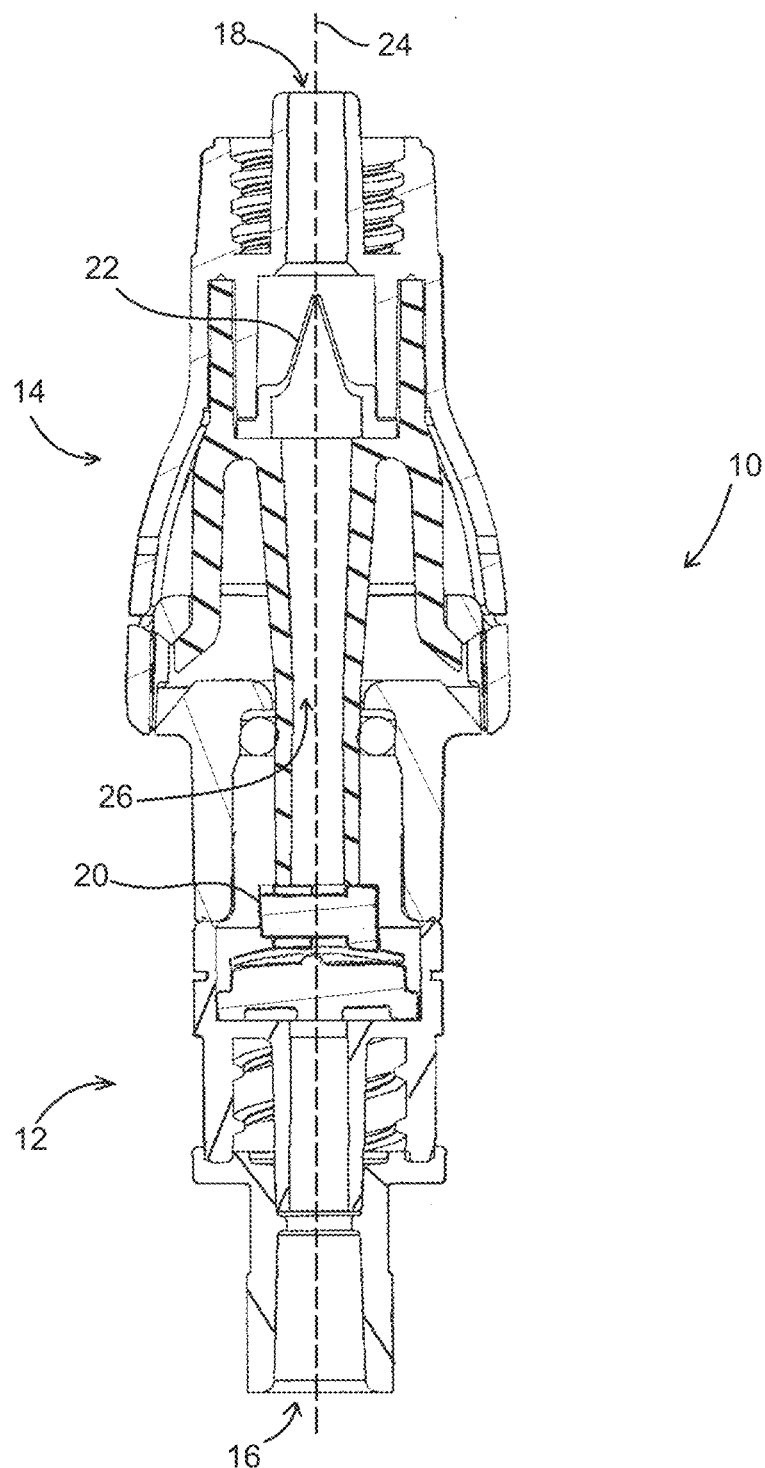
FIG. 4 is a sectional side view of an embodiment of an exemplary apparatus.

FIG. 4 demonstrates an exemplary embodiment of an apparatus 10 where the pump side and patient side members 12, 14 are coupled together such that a fluid, gas, or solid may pass through the apparatus 10 for delivery to a patient 102 at a delivery site 100. For example, a medical provider may be administering a saline solution to a patient 102 through a medical line. A first line 104 may be coupled to a first fitting 13 of the pump side member 12. The saline solution would then enter the apparatus 10 at the flow inlet 16. In one embodiment, a channel 26 disposed about an axis 24 runs through the pump side and patient side members 12, 14 when the pump side and patient side members 12, 14 are coupled together. The saline solution flows through the pump side member 12 to the patient side member 14 via the channel 26. A second line 106 may be coupled to a second fitting 15 of the patient side member 14. The saline solution would then flow out of the patient side member 14 and the apparatus 10 via the flow outlet 18 into the second line 106 which would then deliver the saline solution to the patient 102 via the delivery site 100.

In some embodiments, the apparatus 10 includes at least one valve to prevent the flow of fluids, gases, or solids when the pump side member 12 is decoupled from the patient side member 14. In one embodiment, a first valve 20 is disposed within the pump side member 12. The first valve 20 may comprise an active valve. The active valve 20 is configured to allow fluids to pass through the active valve 20 when the pump side and patient side members 12, 14 are coupled. Thus, when the pump side and patient side members 12, 14 are coupled, the active valve 20 is activated and fluids may pass through the pump side member 12 and when the pump side and patient side members 12, 14 are decoupled, the active valve 20 is not activated and fluids may not pass through the pump side member 12. This prevents a loss of fluids from occurring in the instance of a disconnect, whether accidental or purposeful. One of skill in the art would readily appreciate that a variety of active valves may be implemented in this embodiment, including a QOSINA™ check valve.

A second valve may be disposed within the patient side member 12. The second valve 22 may comprise a passive valve. The passive valve 22 may be configured to allow flow to occur in one direction. The passive valve 22 may also be described as a unidirectional valve. When fluids are being pushed through the apparatus 10 from the pump side member 12 to the patient side member 14, fluids are able to freely flow through the passive valve 22. However, if fluids are somehow being forced through the apparatus 10 in an opposite direction from what was previously described, the fluids are unable to pass through the passive valve 22 in the opposite direction. This prevents the loss of fluids from occurring in the instance of a disconnect, whether accidental or purposeful. This also prevents a backflow of fluids from a patient 102 to the pump side member 12 and the first line 104. A backflow of fluids from a patient 102 may occasionally occur, including instances in which an IV delivery bag has been exhausted and a small portion of blood and other fluids travel away from the patient 102, either due to forces exerted by pressure gradients or diffusion. Fluids traveling from the patient into the first and second lines 104, 106 contaminate the lines 104, 106 such that the lines need to be replaced. With a passive valve 22 or unidirectional valve disposed in the patient side member 14, fluids are unable to move in a reverse direction and contaminate the pump side member 12 and the first line 104. One of skill in the art would readily appreciate that a variety of unidirectional or passive valves may be implemented in this embodiment, including a duckbill valve.

Figure 5:
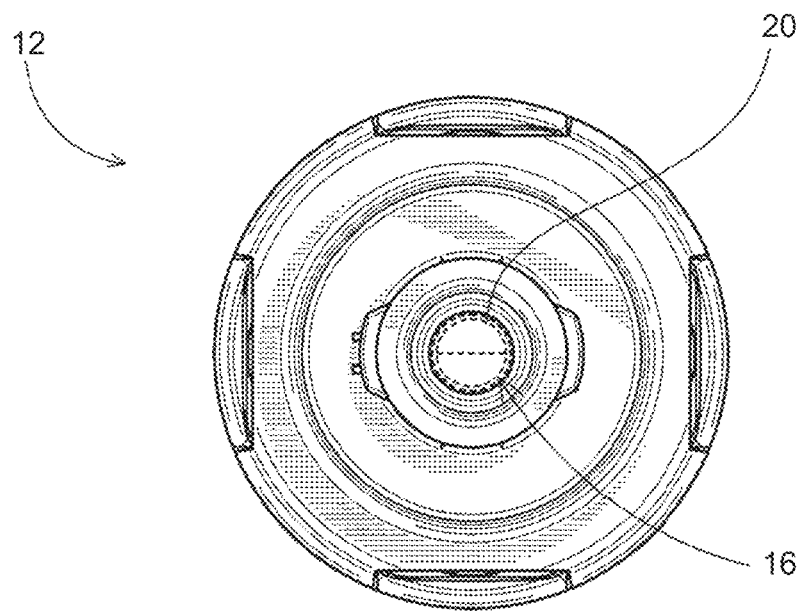
FIG. 5 is a frontal view of an exemplary pump side member having a first valve disposed in the pump side member.
Figure 6:
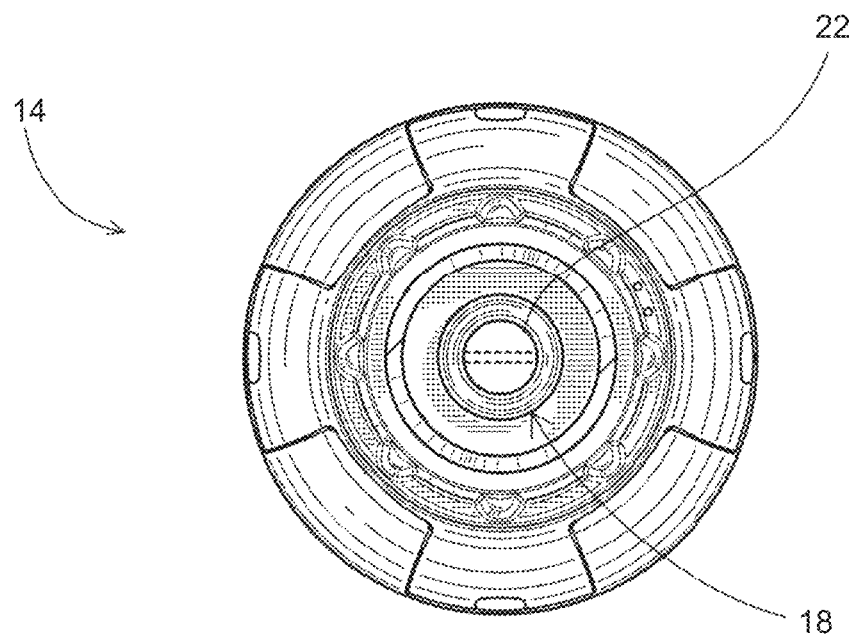
FIG. 6 is a frontal view of an exemplary patient side member having a second valve disposed in the patient side member

FIG. 5 demonstrates an exemplary embodiment in which a first valve 20 is disposed in the pump side member 12 of the apparatus 10. FIG. 6 demonstrates an exemplary embodiment in which a second valve 22 is disposed in the patient side member 14 of the apparatus 10.

Figure 7:
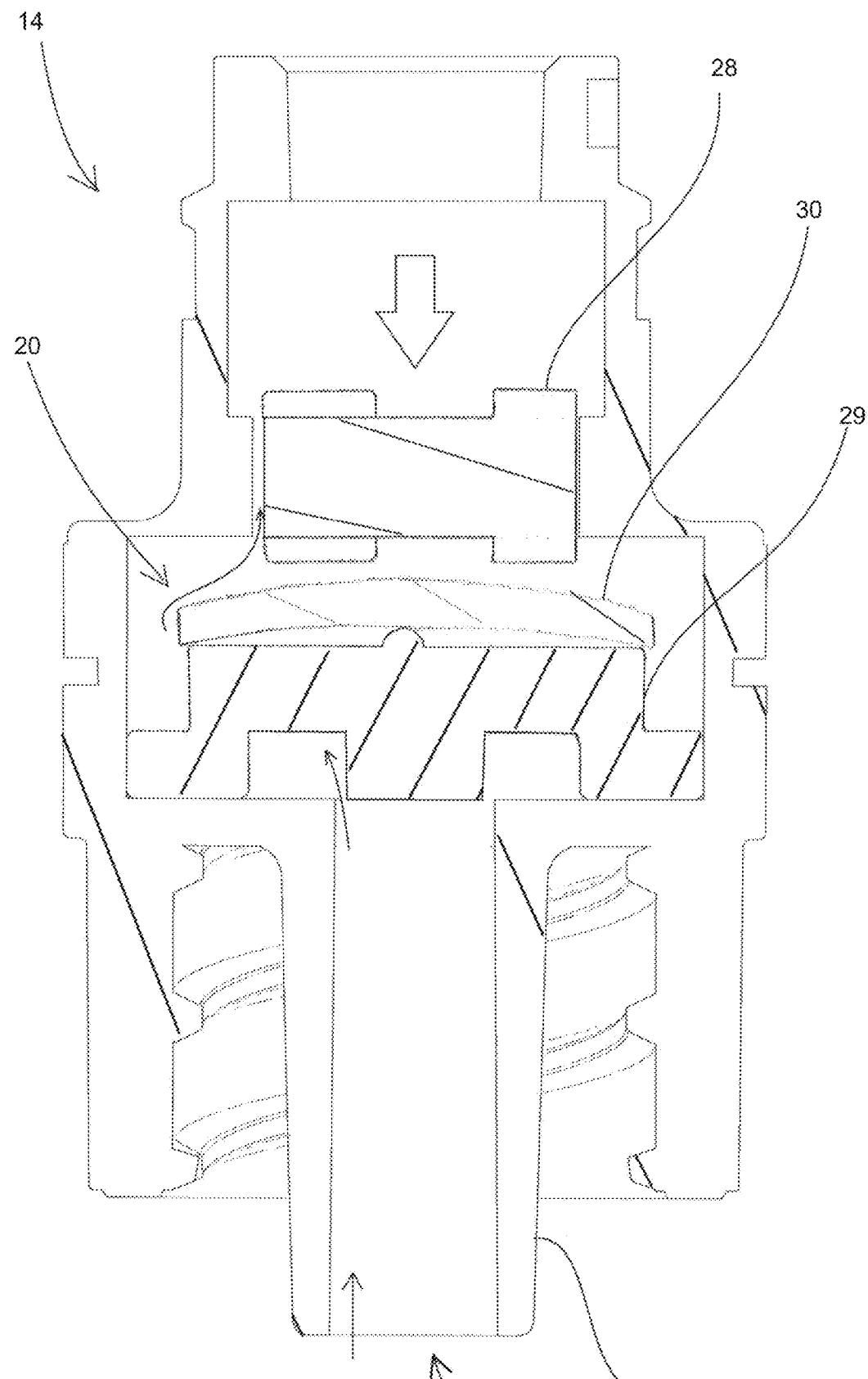
FIG. 7 is a sectional side view of an exemplary embodiment of a first valve disposed in a pump side member.

FIG. 7 provides a representation of an exemplary first valve 20 disposed in a first valve chamber 21 of the pump side member 12 of the apparatus 10. In this embodiment, the first valve 20 is an active valve. The first valve 20 comprises a piston 28, a support base 29, and a diaphragm 30. When the first valve 20 is not activated, the diaphragm 30 forms a seal with the inner wall 31 of the pump side member 12 such that fluid is unable to pass through the pump side member 12. The piston 28 may be manually biased toward the diaphragm 30 such that the diaphragm 30 biases away from the inner wall 31 and breaks the seal between the diaphragm 30 and the inner wall 31. When the diaphragm 30 is biased away from the inner wall 31, fluid is able to flow past the diaphragm 30, past the piston 29, and through the pump side member 12. The diaphragm 30 may rest on a support base 29 within the first valve chamber 21. The support base 29 may be configured to permit fluids to pass from the flow inlet 16 into the first valve chamber 21. The support base 29 may also be configured to bias the diaphragm 30 toward the inner walls 31 of the pump side member 12 when the piston 28 is not exerting a force on the diaphragm 30, thus creating a seal between the diaphragm 30 and the inner walls 31. The seal between the diaphragm 30 and the inner walls 31 may also be a result of fluids being forced from a pump into the pump side member 12 and pressing the diaphragm 30 against the inner walls 31. The seal may be a result of both forces previously discussed.

Figure 8:
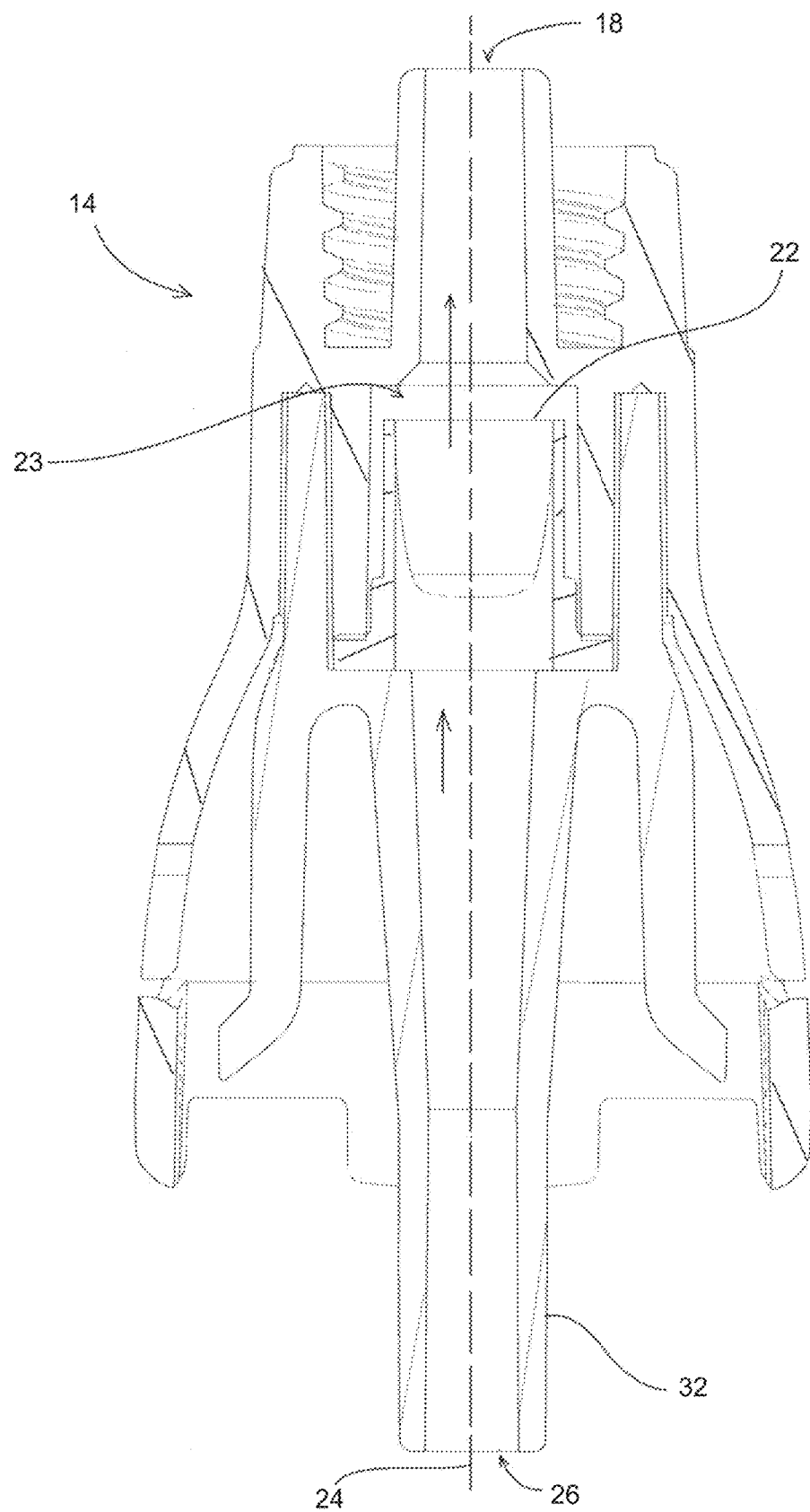
FIG. 8 is a sectional side view of an exemplary embodiment of a second valve disposed in a patient side member.

Now referring to FIG. 8, an exemplary embodiment of a patient side member 14 disposed about an axis 24 is depicted. The patient side member 14 further comprises a stem or cannula 32, a second valve chamber 23, a flow outlet 18, and a channel 26 running through the patient side member 14. A second valve 22 may be disposed in the second valve chamber 23. The second valve 22 may be a unidirectional valve or more specifically a duckbill valve, permitting fluids to travel through the second valve 22 in a single direction. In one embodiment, the cannula 32 extends from the second valve chamber 23 and the flow outlet is disposed at or near the second valve chamber 23 opposite the cannula 32. In this embodiment, a fluid may enter the cannula 32 and travel through the channel 26 to the second valve chamber 23. The second valve 22 disposed in the second valve chamber 23 is configured to permit fluid to flow from the cannula-portion of the channel 26 to the flow-outlet portion of the channel 18. The fluid then passes out of the patient side member 14 of the apparatus 10. The fluid moving from the cannula portion of the channel 26 creates internal pressure on the duckbill valve, causing the valve to open. When fluids are travelling in an opposite direction, from the flow outlet-portion of the channel 18, external pressure on the duckbill valve causes the valve to seal shut.

Figure 9:
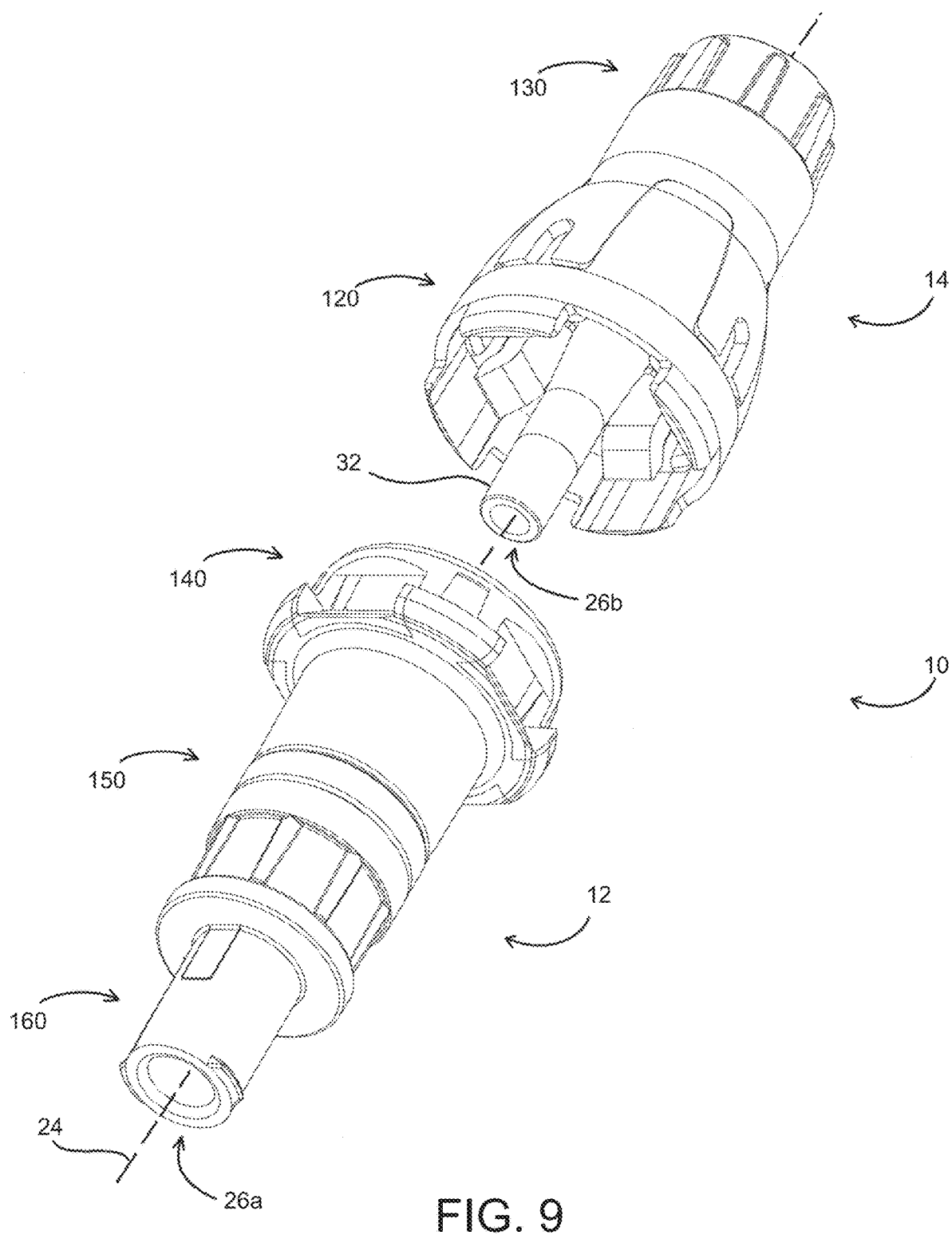
FIG. 9 is perspective view of an exemplary embodiment of pump side member and a patient side member when uncoupled.
Figure 10:
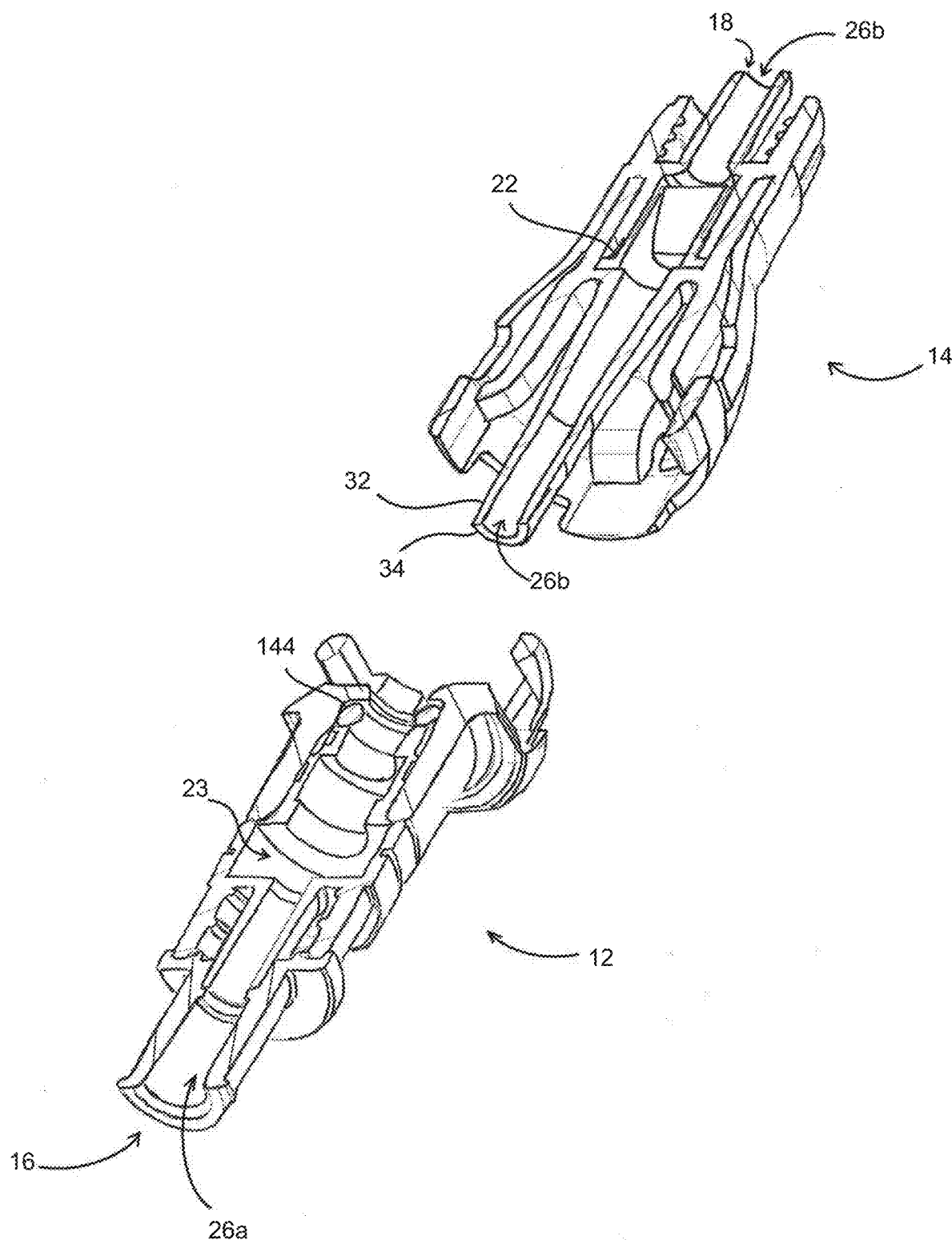
FIG. 10 is sectional perspective view of an exemplary embodiment of pump side member and a patient side member when uncoupled.

FIGS. 9 and 10 demonstrate an embodiment in which various components are coupled together to form a pump side member 12 and a patient side member 14. In some embodiments, the pump side member 12 may comprise a female luer lock adaptor 160, a luer activated check valve housing 150, and a snap fit connector 140. In some embodiments, the female luer lock 160, the luer activated check valve housing 150, and the snap fit connector 140 may be integrated into a single unit. The patient side member 14 comprises an anti-reconnection device 120 and a key slot device 130. In some embodiments, the anti-reconnection device 120 and the key slot device 130 may be integrated into a single unit. Each of these elements and various embodiments will be discussed in more detail below.

Figure 11:
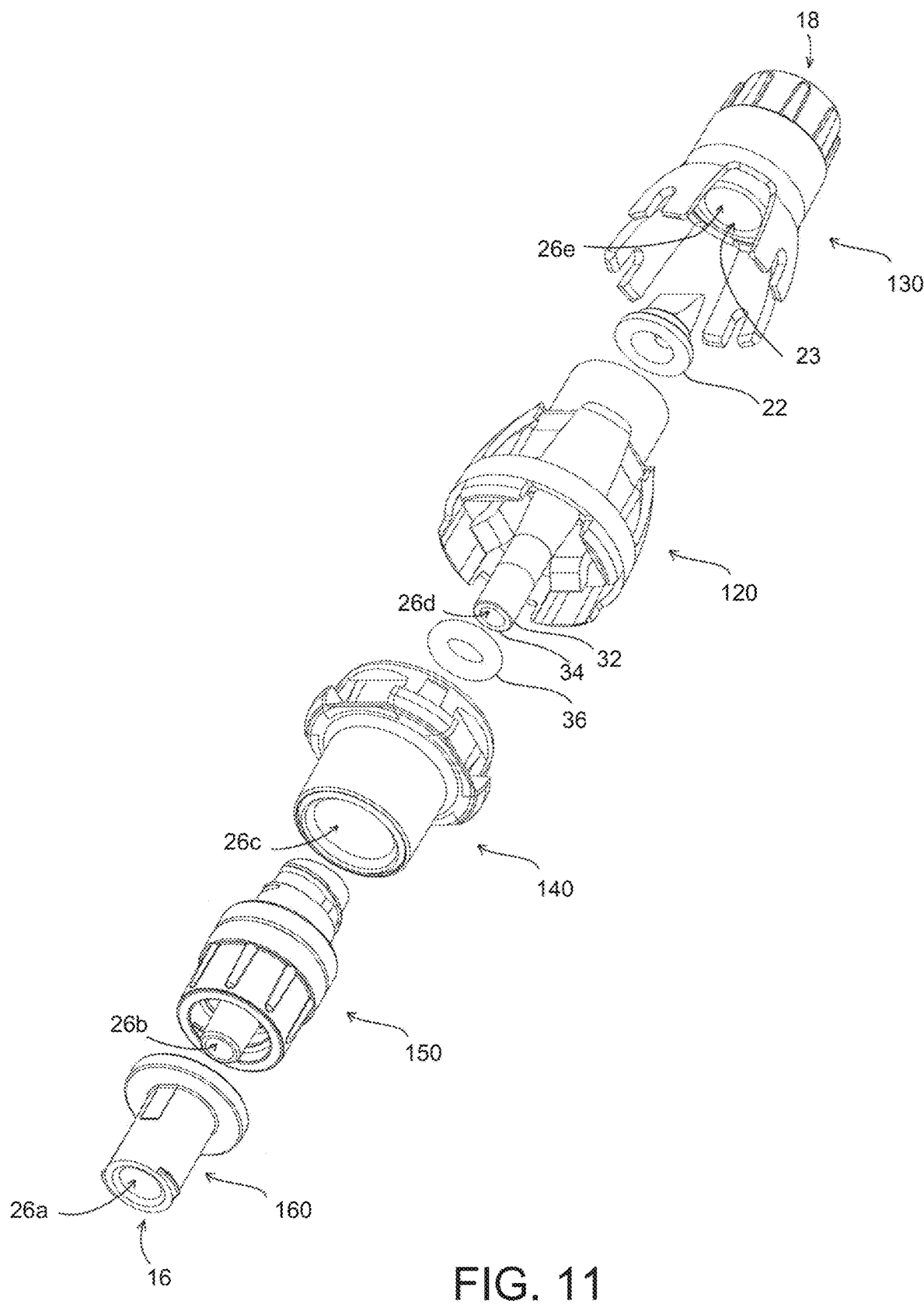
FIG. 11 is an exploded perspective view of an exemplary embodiment of an apparatus.

In one embodiment, the cannula 32 of the patient side member 14 extends from the patient side member 14. A channel 26b disposed about an axis 24 may run through the cannula 32 and the patient side member 24. When the cannula 32 is inserted into the pump side member 12, the channel 26a of the pump side member 12 is in a sealed configuration with the channel 26b of the patient side member 14. When the pump side member 12 and the patient side member 14 are comprised of the various elements previously recited as shown in FIG. 11, each element has an individual channel 26a-26e that, when each of the elements is coupled together in a sealed configuration, forms a single channel 26 through which a fluid may flow through the apparatus 10. The various components may remain separate or they may be manufactured in a variety of combinations of unitary components excepting the snap fit connector 140 and the anti-reconnection device 120.

Figure 12:
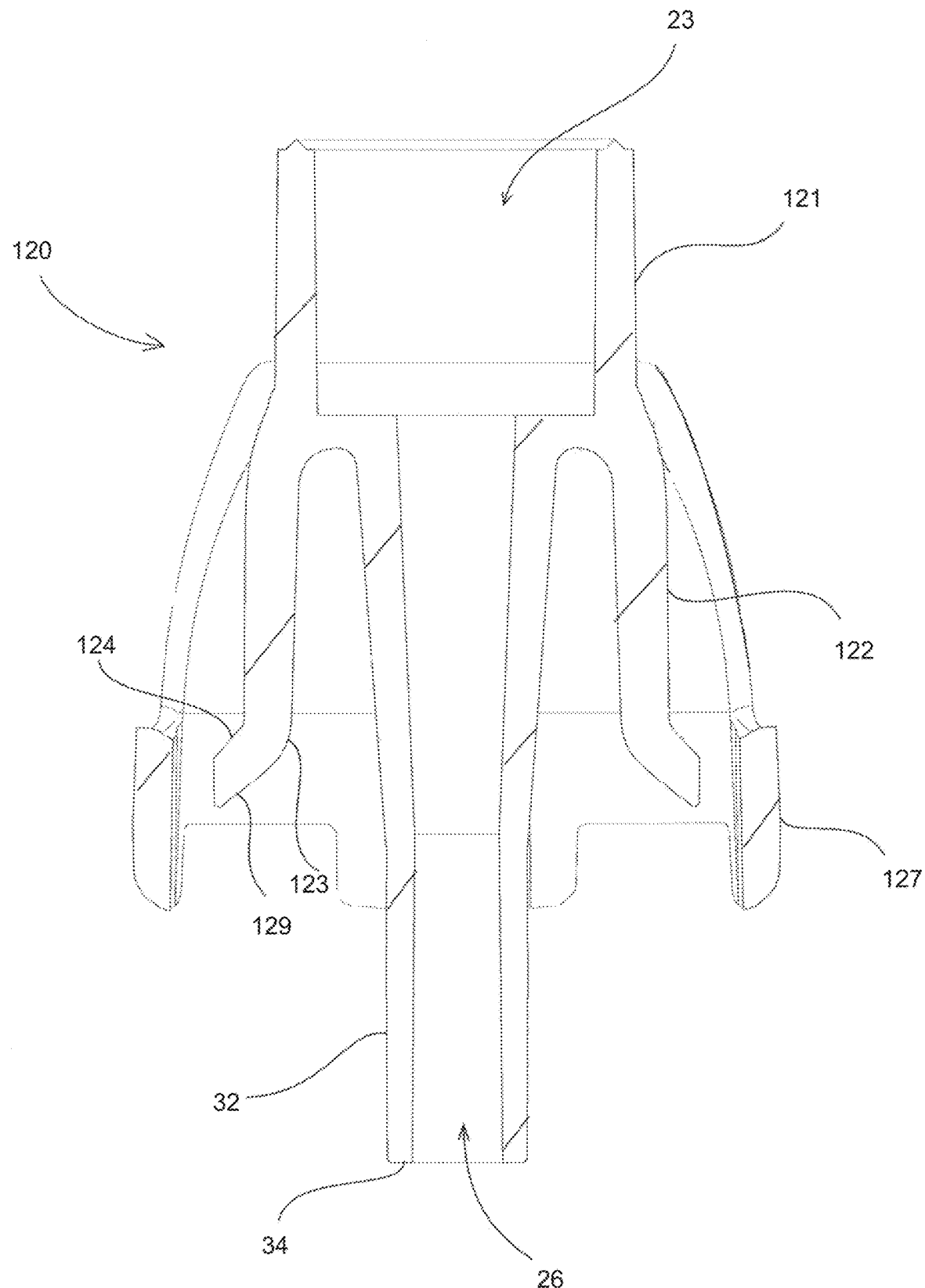
FIG. 12 is a sectional side view of an exemplary embodiment of an anti-reconnection device.

FIG. 12 demonstrates an embodiment of an anti-reconnection device 120. The anti-reconnection device 120 comprises a neck 121 and a stem or cannula 32. A channel 26 passes through both the neck 121 and the cannula 32. The channel 26 and the anti-reconnection device 120 may be disposed about an axis 24. In one embodiment, the neck 121 defines a second valve chamber 23 into which a second valve 22 may be placed to control the flow and the direction of flow of liquids through the apparatus 10. Many varying valves may be placed in the chamber, but one embodiment includes a duckbill valve to control the direction of flow of liquids in the apparatus 10.

Figure 17A:
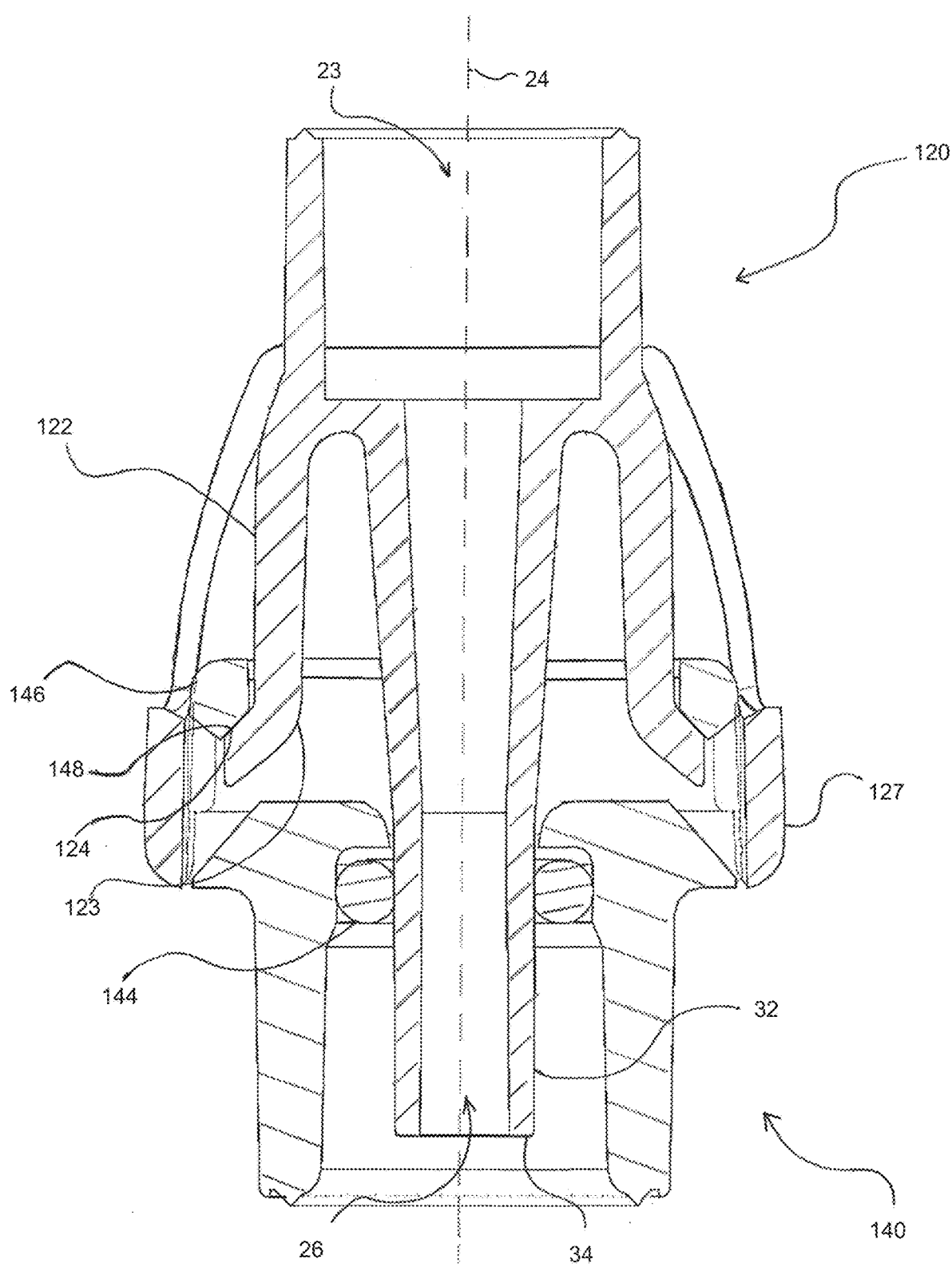
FIG. 17a-f is a sectional side view of an embodiment of a snap fit connector and an anti-reconnection device as axial force is applied to the apparatus.
Figure 17B:
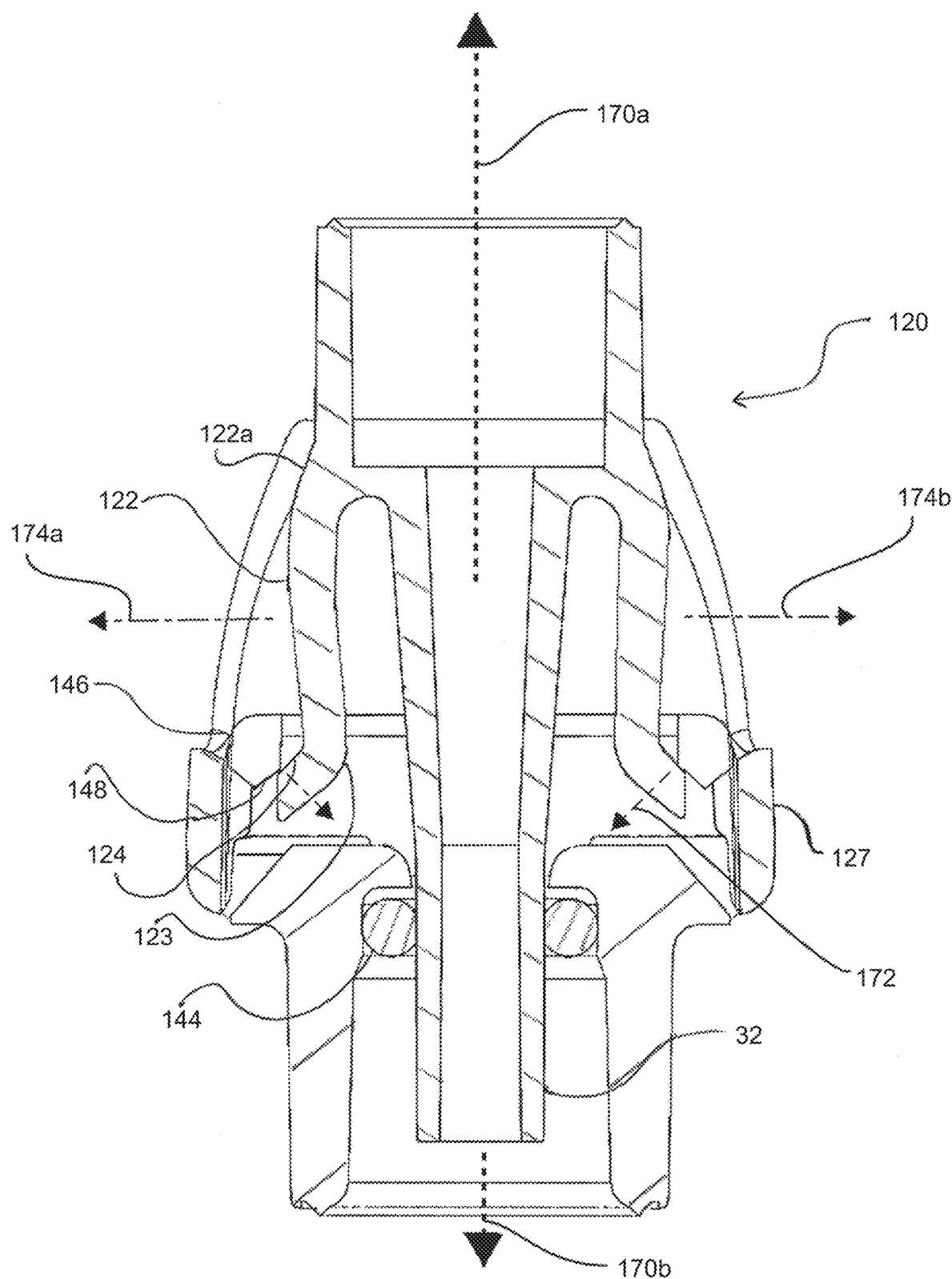
Figure 17C:
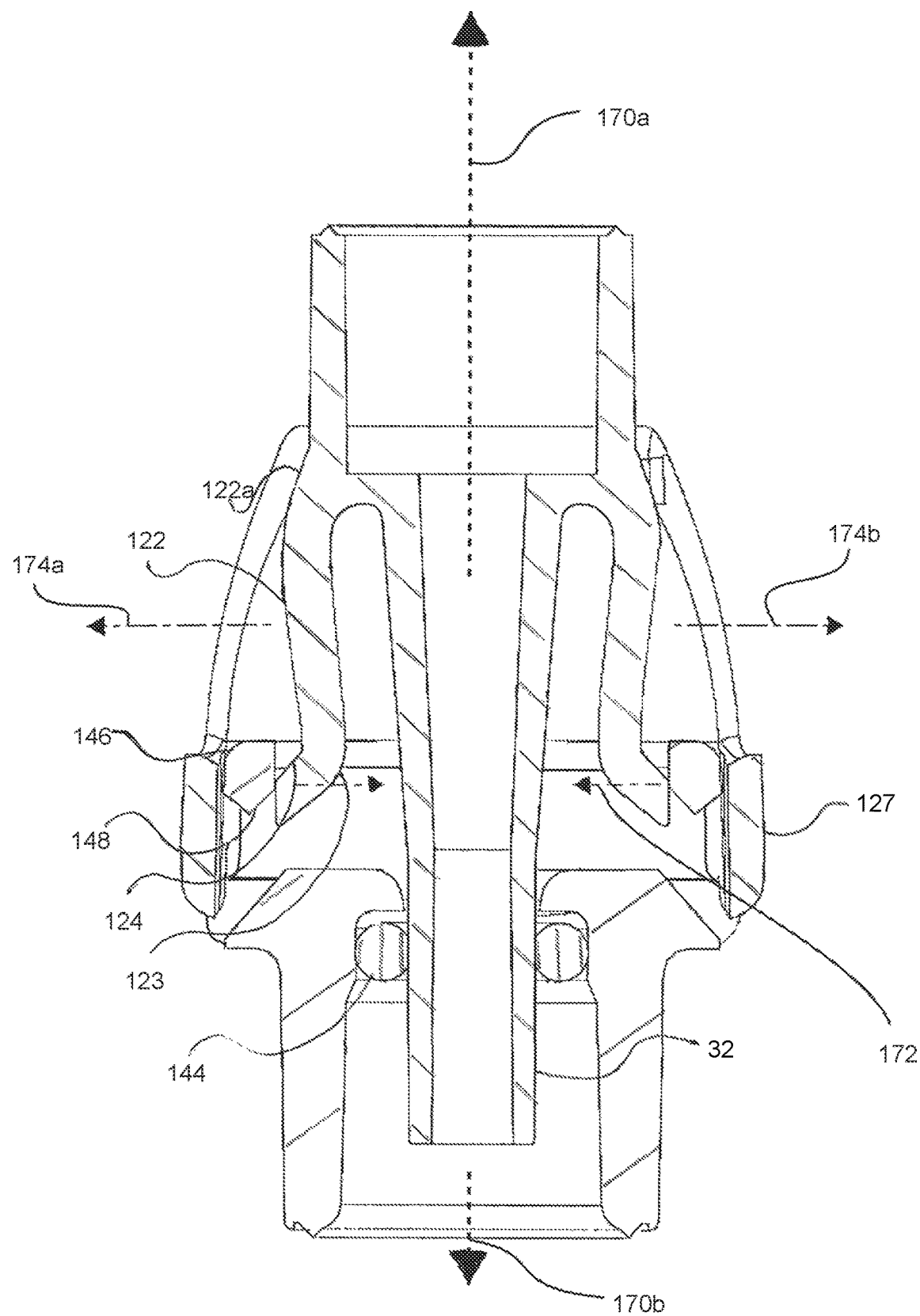
Figure 17D:
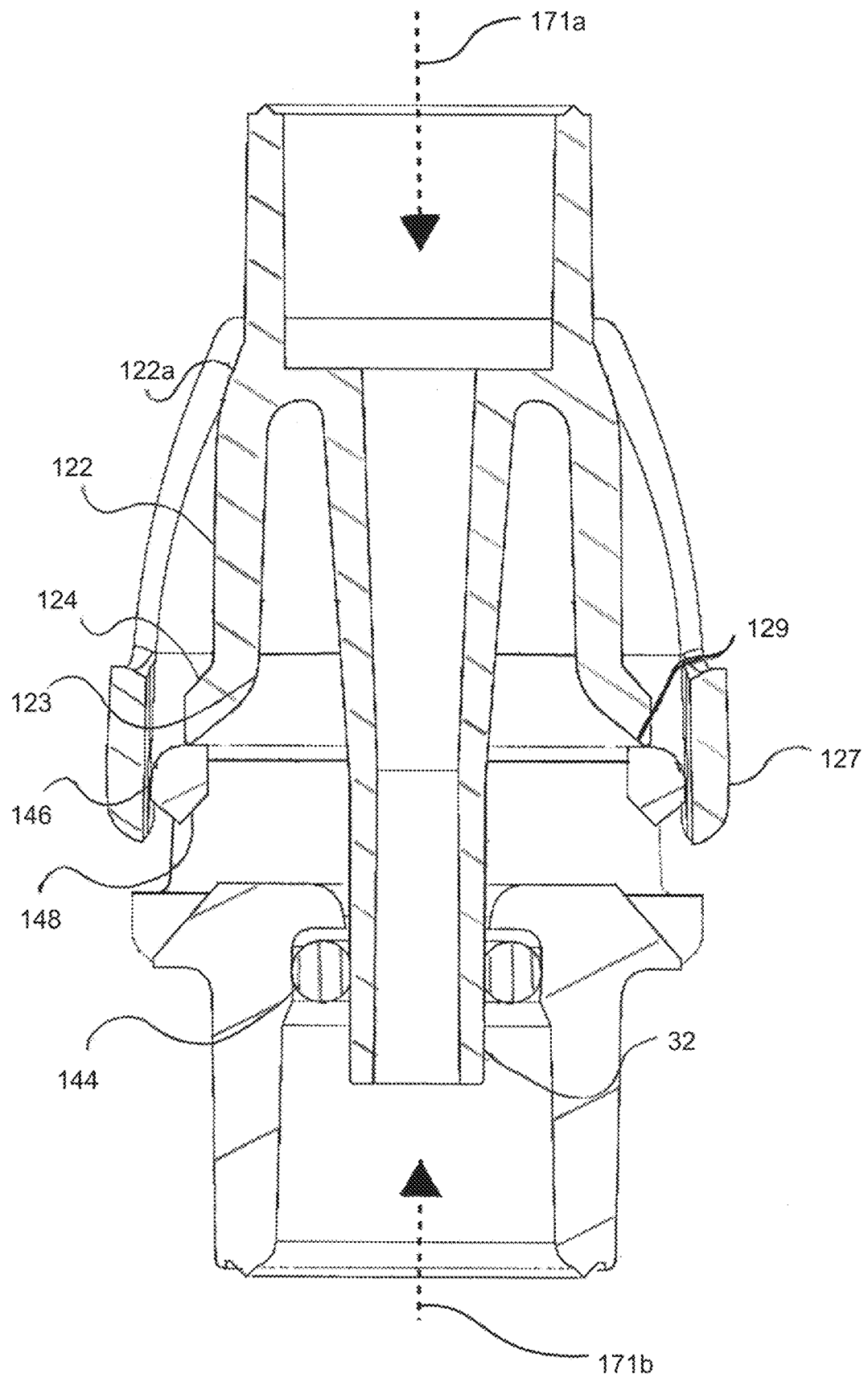
Figure 17E:
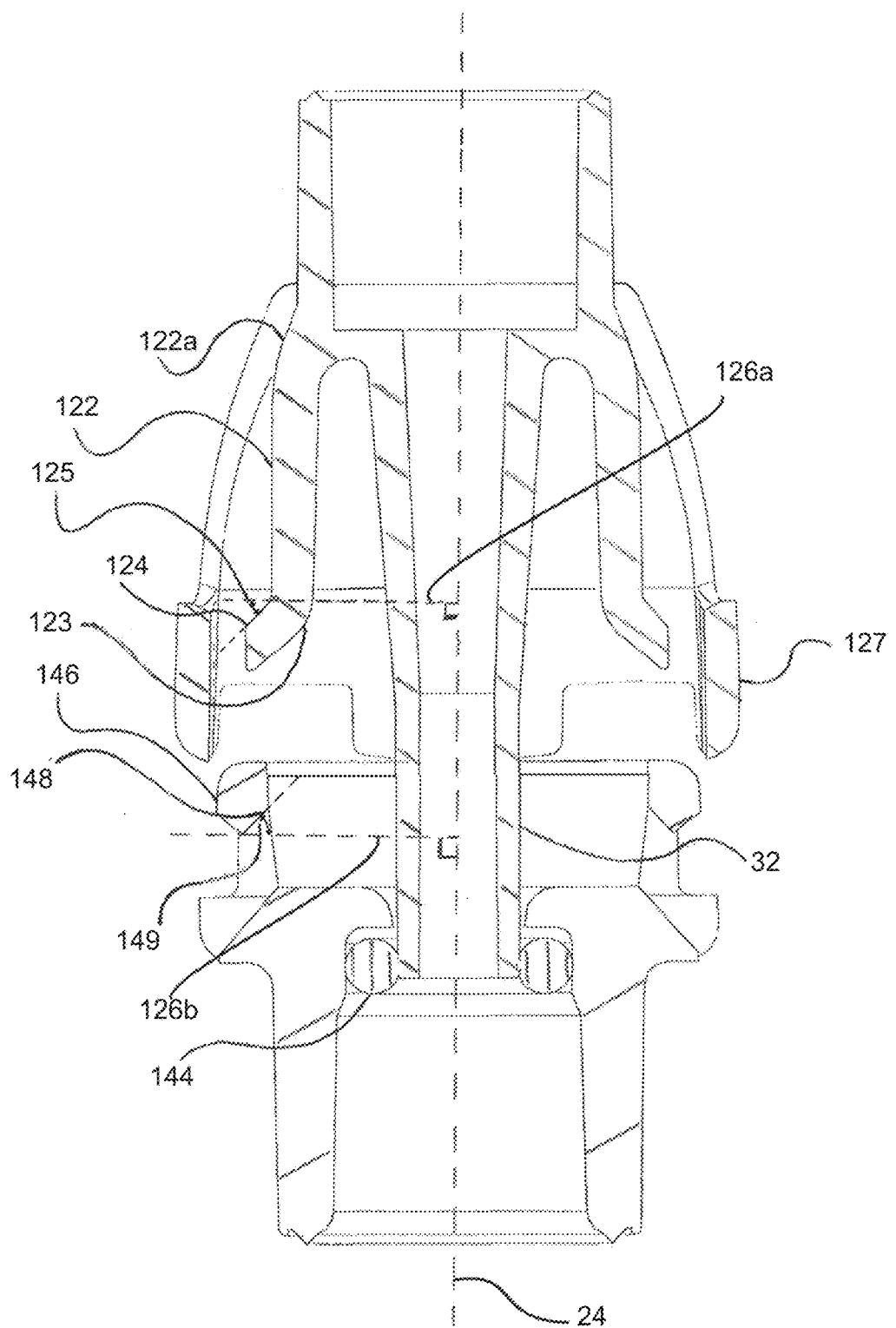
Figure 17F:
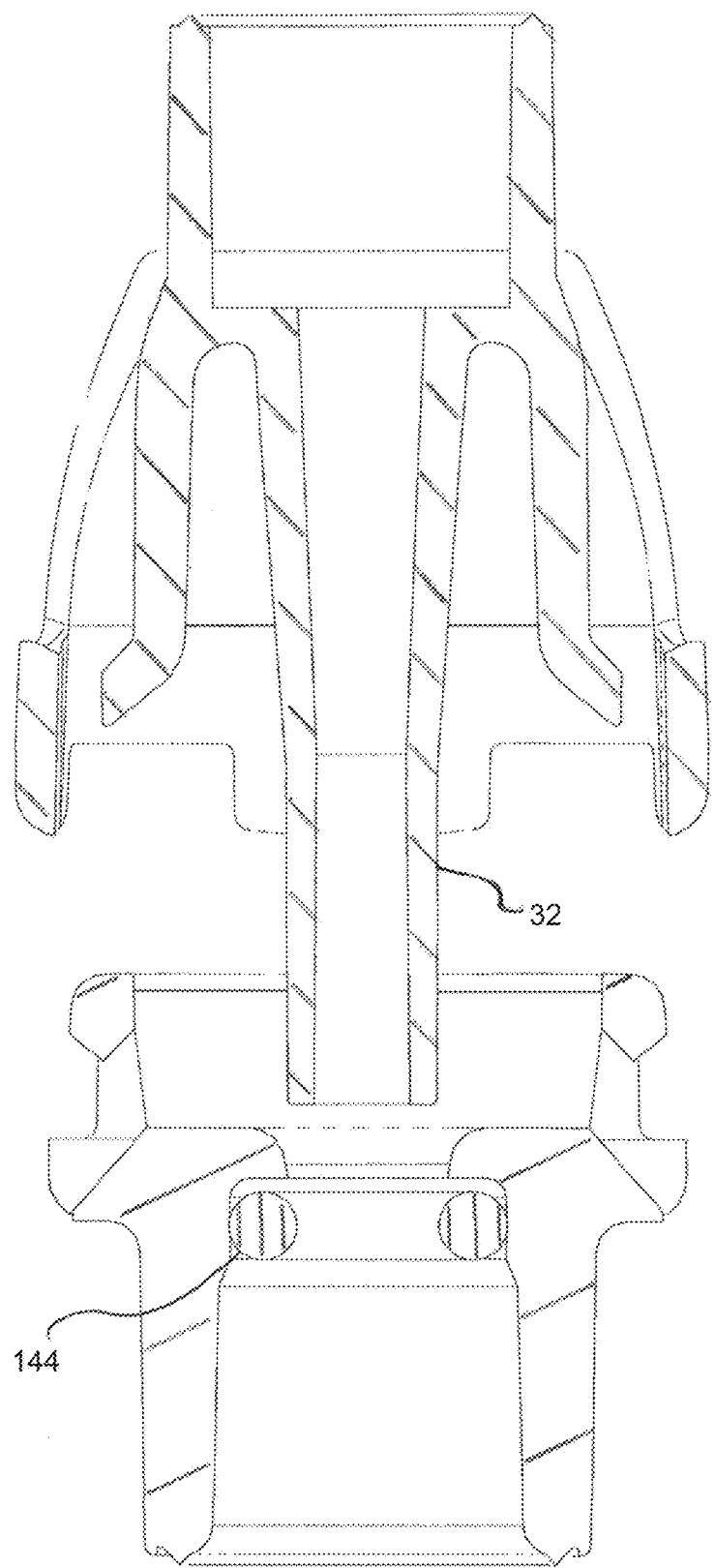
Figure 18A:
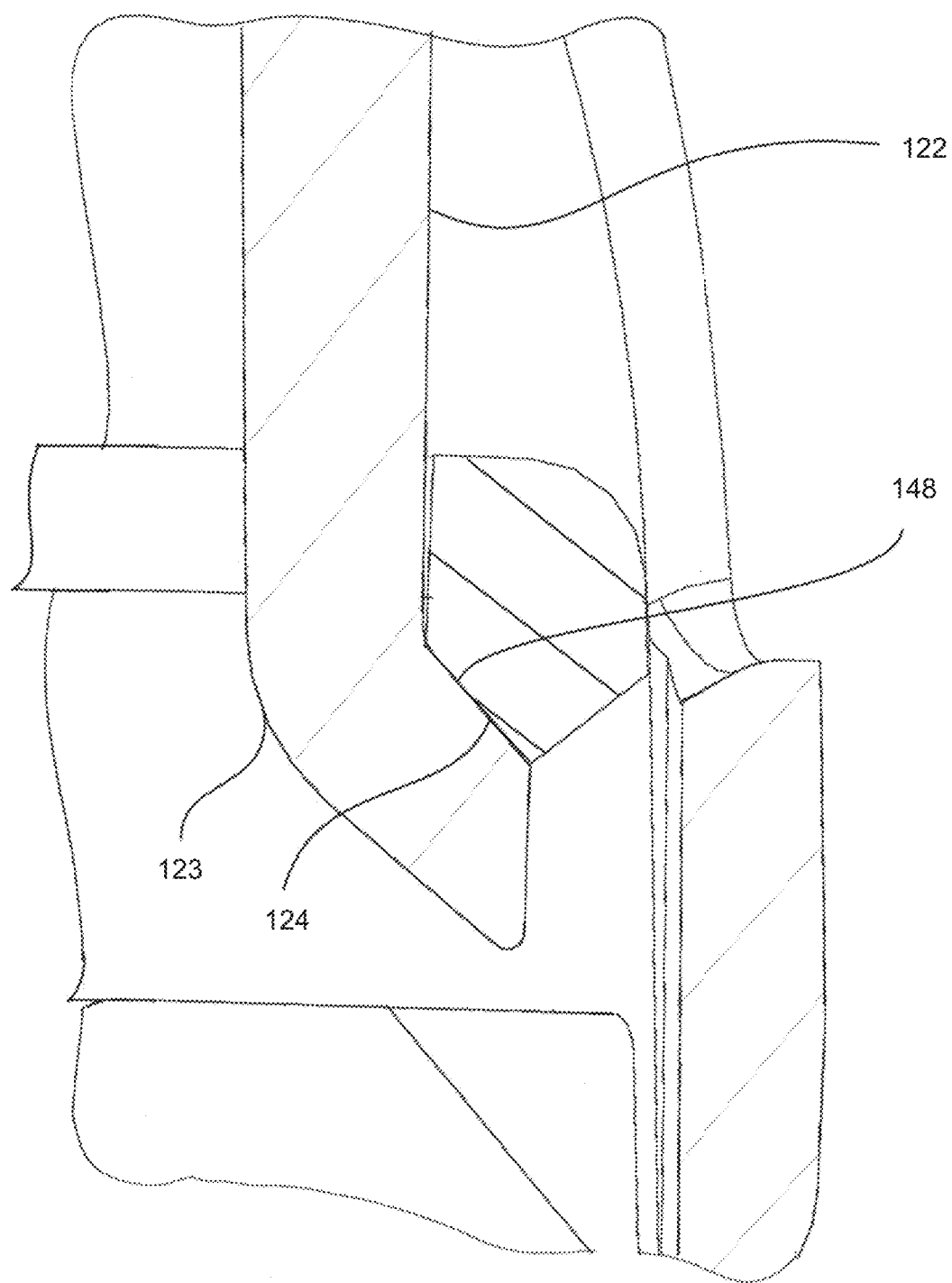
FIG. 18a-e is a close-up sectional side view of an embodiment of a snap fit connector and an anti-reconnection device as axial force is applied to the apparatus.
Figure 18B:
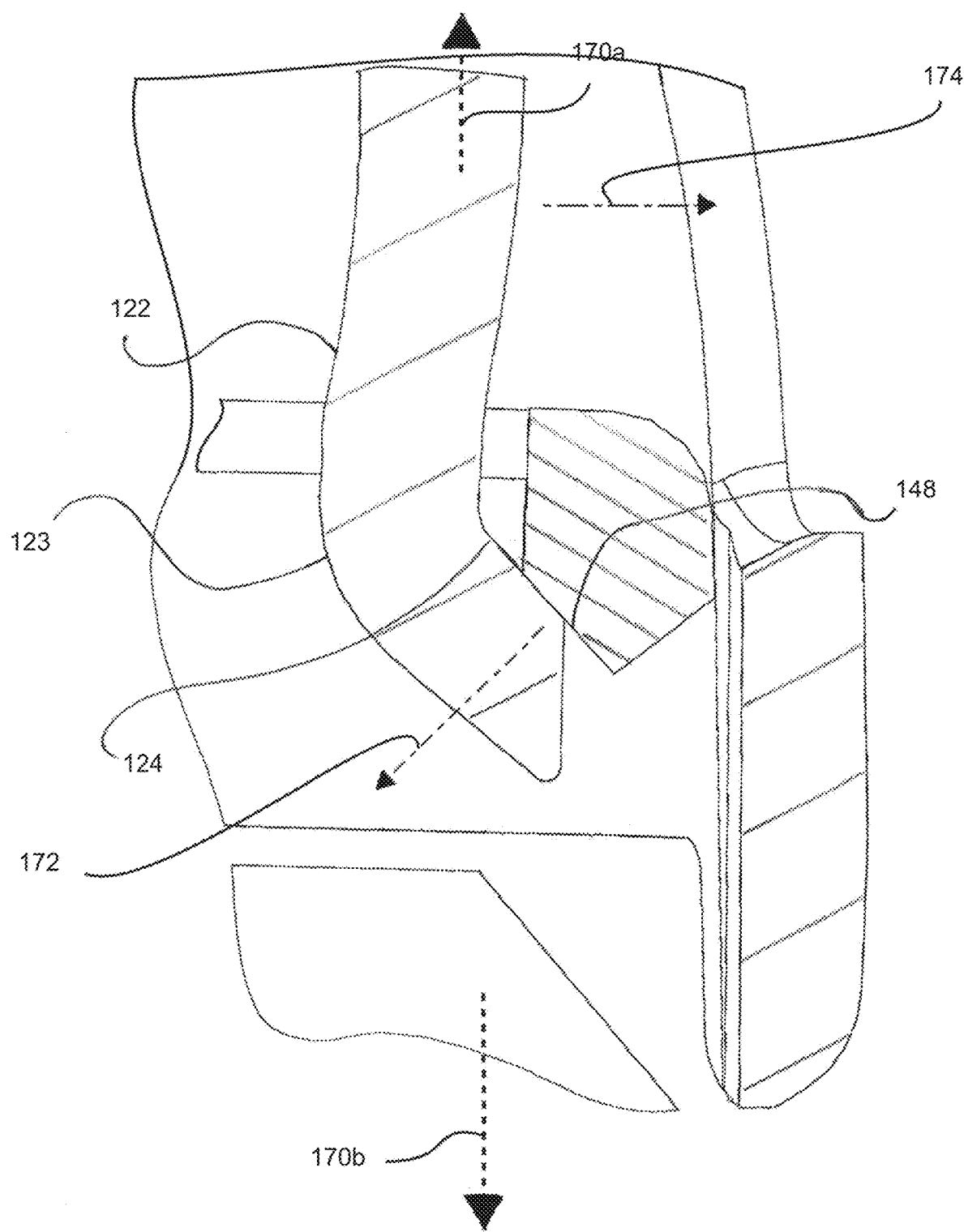
Figure 18C:
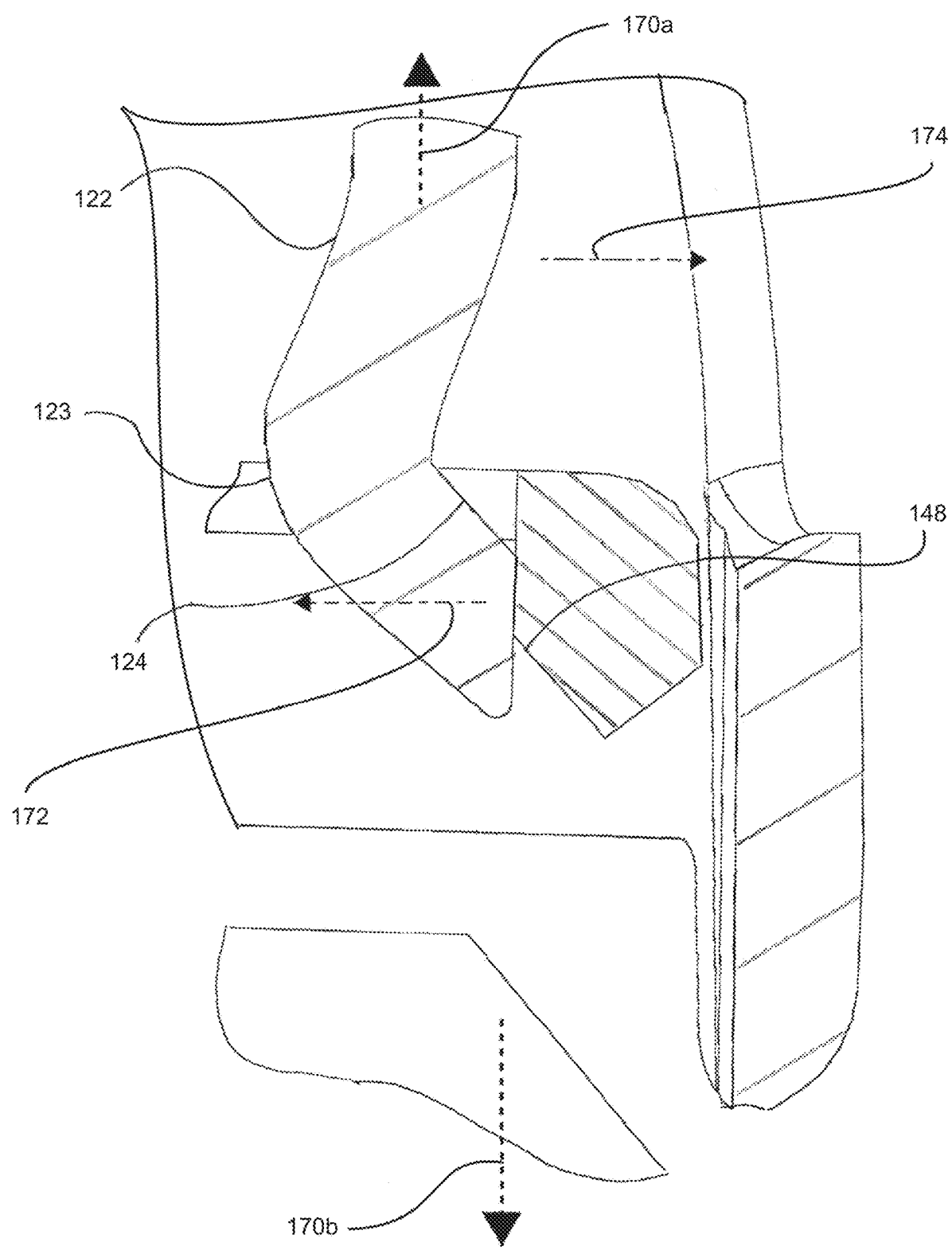
Figure 18D:
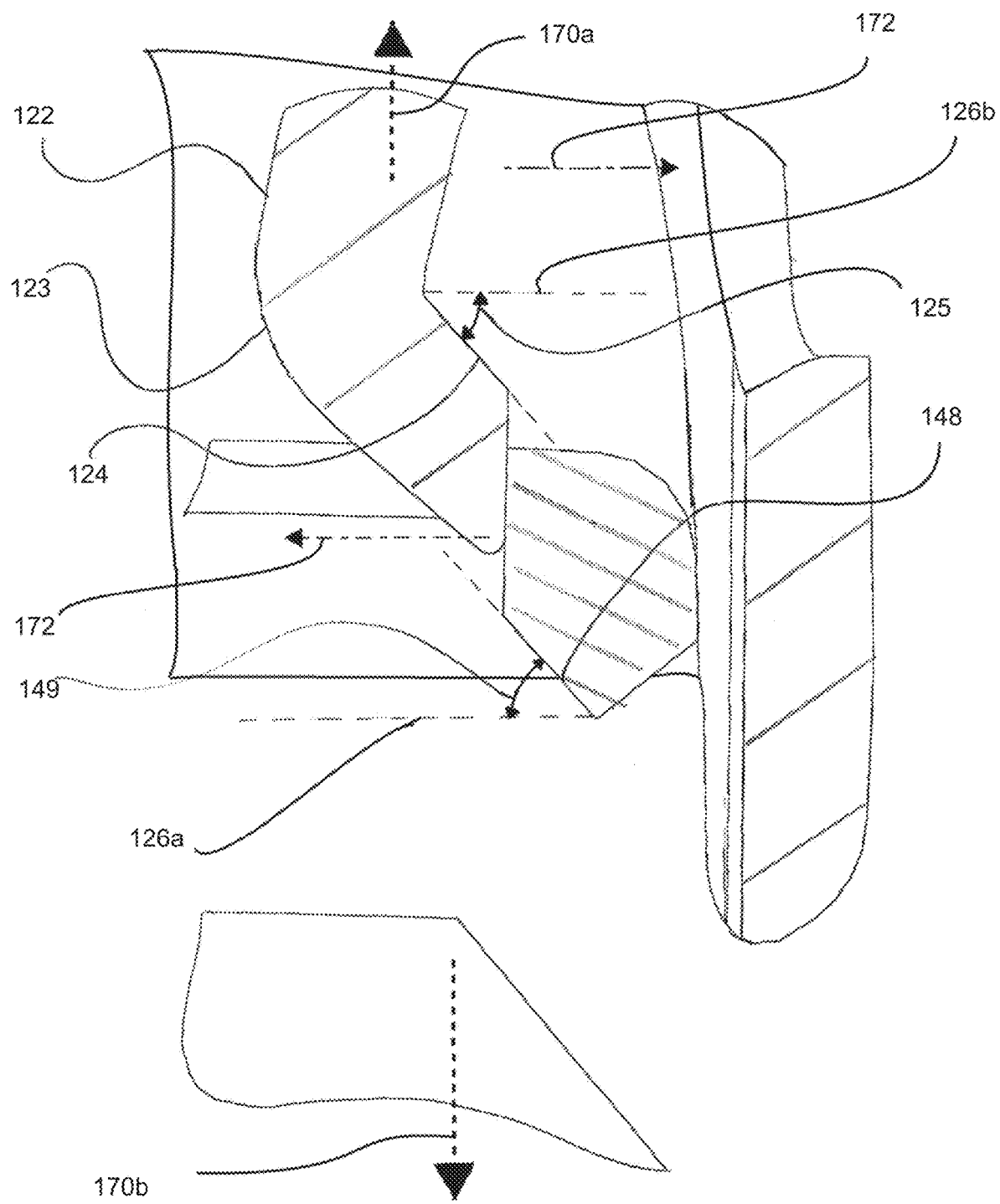

An anti-reconnection device 120 may further comprise at least one securing arm 122. The securing arm 122 is configured to allow the apparatus 10 to detachably couple, thus allowing a medical line to release when a force is applied to the medical line across the apparatus 10. In some embodiments the securing arm 122 extends from the anti-reconnection device 120 at a distal end of the neck 121. The securing arms 122 extend from the neck 121 such that the securing arms 133 are located radially outward from the cannula 32. In some embodiments, the securing arms 122 may be substantially perpendicular to the axis 24. At a distal end of the securing arms 122, a securing joint 123 defines a bend at which the securing arms 122 are no longer parallel with the axis 24 and begin extending radially outward from the axis 24 at an angle greater than 90 degrees. Thus, a gripping surface 124 extending from the securing arms 122 at the securing joint 123 is at an angle 125 less than 90 degrees relative to a radial axis 126 extending perpendicularly from the first axis 24 running through the channel 26. See FIGS. 17e and 18d.

Another embodiment of the anti-reconnection device 120 may include a shield 127. The shield 127 may be disposed radially outward from the gripping surface 124 and in other embodiments about the securing arms 122. The shield 127 prevents the securing arms 122 from being intentionally or unintentionally contacted by a patient or otherwise. In some embodiments, the shield 127 defines securing arm guard receiving slots 128. The securing arm guard receiving slots 128 are configured to receive securing arm guards 136 which will be further described hereinafter.

Figure 13:
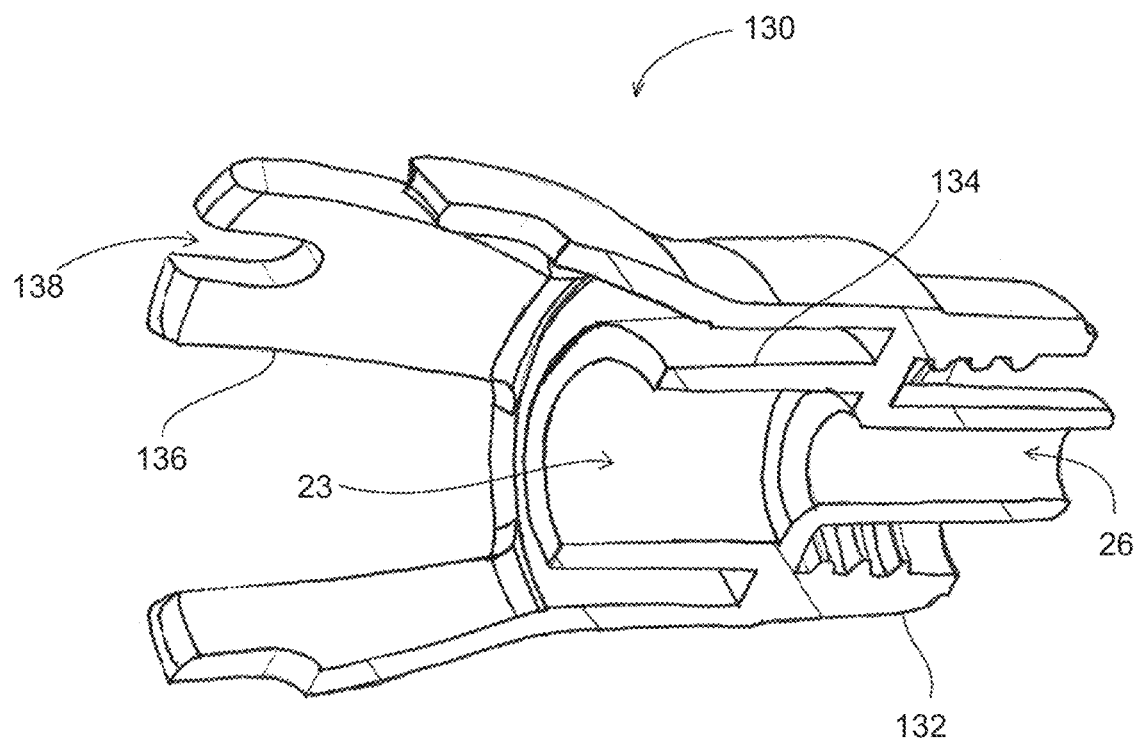
FIG. 13 is a sectional perspective view of an exemplary embodiment of a key slot device.

FIG. 13 demonstrates an embodiment of a key slot device 130. The key slot device 130 substantially corresponds to an anti-reconnection device 120 to form the patient side member 14. In one embodiment, the key slot device 130 may comprise a male luer lock 132 having chamber walls 134 extending from a distal end of the male luer lock 132, the chamber walls 134 defining a second valve chamber 23. In some embodiments, the second valve chamber 23 of the anti-reconnection device 120 and the second valve chamber 23 of the key slot device 130 are the same chamber. The walls of each of the anti-reconnection device 120 and the key slot device 132 may correspond in such a way that they form a single second valve chamber 23 as is demonstrated in FIG. 14. A second valve 22 may be inserted into the second valve chamber 23 to regulate the flow and the direction of flow of fluids in the apparatus 10.

The key slot device 130 is disposed about an axis 24 which corresponds with the axis 24 about which anti-reconnection device 120 is disposed, such that when the key slot device 120 and the anti-reconnection device 120 are coupled, there is a single axis 24 about which the patient side member 14 is disposed. Channel 26 runs through key slot device 120.

In some embodiments the key slot device 130 further comprises securing arm guards 136. The securing arm guards 136 are disposed radially outward from the securing arms 122 of the anti-reconnection device 120 when coupled to the key slot device 130 as demonstrated in FIG. 14. The securing arm guards 136 act as a shield to prevent access to the securing arms 122. The securing arm guards 136 may further define key holes 138. When a medical line becomes disconnected, sometimes a patient or another individual may try to reestablish a connection of the apparatus 10. However, this can be dangerous for the patient as the lines may have become contaminated during the disconnection. Thus, when establishing a connection, because the securing arm guard 136 and the shield 127 interfere with direct access to the securing arm 122, the securing arm 122 is inaccessible. The securing arms 122 may only be accessed via the key holes 138 that may be disposed on the securing arm guard 136 or the shield 127. The key holes 138 may be configured such that the only way to access the securing arms 122 is using a special tool designed for the key holes 138. This limits the ability to establish a connection between the pump side and patient side members 12, 14 and ultimately the connection between the IV and the patient 102. Thus, when accidental disconnections do occur, a medical professional may properly evaluate the situation to determine if it is necessary to provide a new connection because of contamination.

Figure 14:
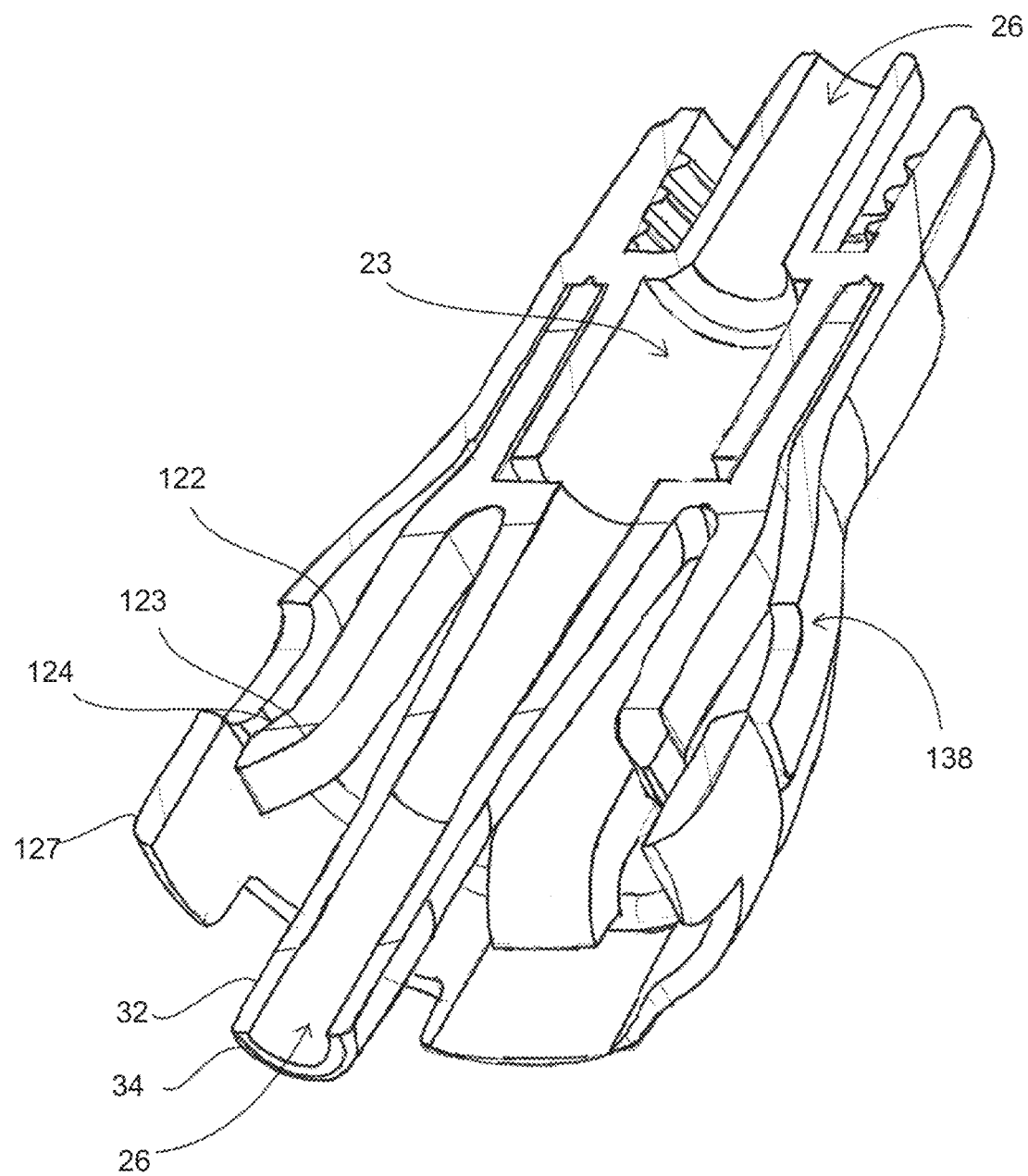
FIG. 14 is a sectional perspective view of an exemplary embodiment of a key slot device coupled with an anti-reconnection device.

FIG. 14 demonstrates an exemplary embodiment of the patient side member 14. The patient side member 14 may be manufactured as three separate subparts (duckbill valve 22, anti-reconnection device 120, and key slot device 130). The subparts may be assembled and coupled using common techniques such as bonding materials, connectors, etc. Another embodiment may be implemented as a unitary construction for the subparts. This could include 3-D printing techniques. However, it is to be understood that the concepts disclosed herein do not depend on the patient side member 14 being either multiple subparts assembled or a unitary, singular member.

In order to further understand the apparatus 10, the pump side member 12 will presently be described in more detail. The pump side member 12 provides an attachment point to which the securing arms 122 of the patient side member 14 may couple, thus the pump side member 12 and the patient side member 14 are coupled to form the apparatus 10.

Figure 15:
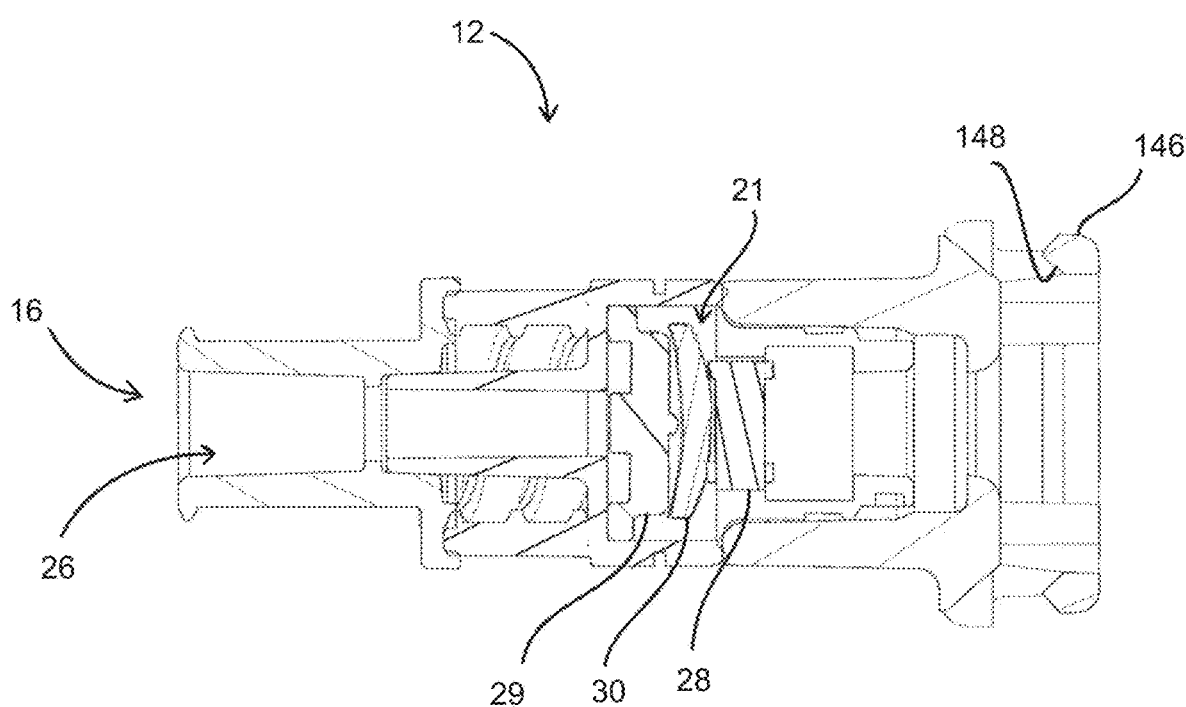
FIG. 15 is a sectional side view of an exemplary embodiment of a pump side member

FIG. 15 discloses an exemplary embodiment of the pump side member 12. In some embodiments, the pump side member 12 may comprise a female luer lock 160, a luer activated check valve device 150, and a snap fit connector 140. Depending on the lines that are being used, the pump side member 12 may comprise different subparts, such as quick connectors, male luer locks, bayonet connectors, compression fittings, barbed connectors, flare connectors, swappable valves, etc. In other embodiment, the pump side member 12 may be a unitary whole and all of the components and functions disclosed by the female luer lock 160, the luer activated check valve device 150, and the snap fit connector 140 may be integrated into a single unit.

Figure 16:
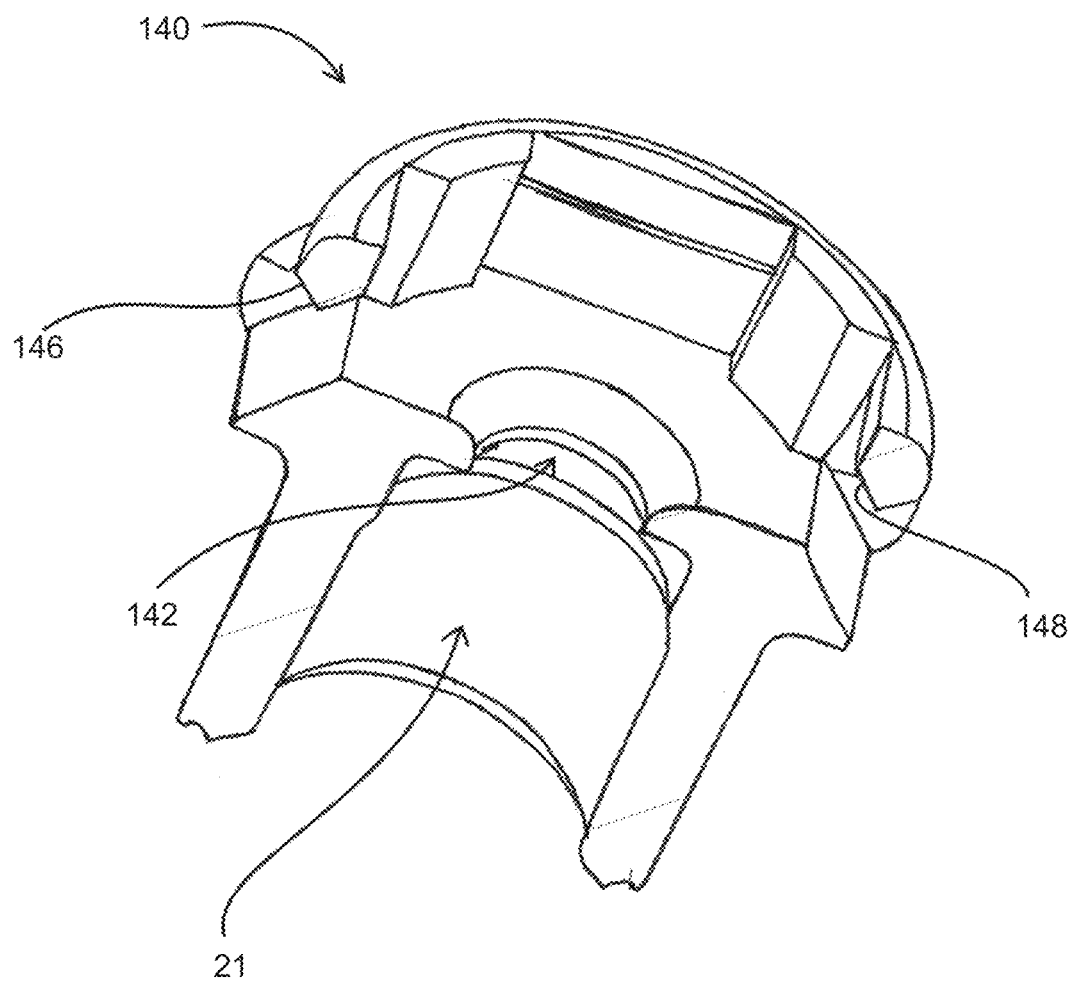
FIG. 16 is a sectional perspective view of an exemplary embodiment of a snap fit connector.

FIG. 16 depicts an exemplary embodiment of a snap fit connector 140. The snap fit connector 140 may be disposed about an axis 24. The axis 24 may run through all of the various subparts of the pump side member 12 when coupled and aligned with the axis 24 of the patient side member 14 and when the pump side member 12 and the patient side member 12 are detachably coupled. Furthermore, a channel 26 may disposed within the snap fit connector 140. When a channel 26 and the patient side member 14 are detachably coupled, the members 12, 14 form a single channel 26.

The snap fit connector 140 may also define a toric joint recess 142. This recess 142 is configured to receive a toric joint 144 to prevent fluid leakage when the members 12, 14 are detachably coupled.

An exemplary embodiment of the snap fit connector 140 may further comprise a securing bar 146. The securing bar 146 is configured to receive the securing arms 122 of the anti-reconnection device 120. In one embodiment, the relationship between the securing arms 122 and the securing bar 146 provide the apparatus 10 with the anti-reconnection and breakaway functionalities.

The securing bar 146 in some exemplary embodiments may further comprise an angled receiving surface 148. The angled receiving surface 148 may be at an angle 149 of less than 90 degrees in relation to a radial axis 126 extending perpendicularly out from the first axis 24. See FIGS. 17e and 18d. The angled receiving surface 148 of the securing bar 146 and the gripping surface 124 of the securing arms 122 are configured to be complimentary to one another. In some embodiments this may result in the angled receiving surface 148 and the gripping surface 124 being flush when the pump side and patient side members 12, 14 are detachably coupled. Thus, when the pump side and patient side members 12, 14 are detachably coupled, the gripping surface 124 and the angled receiving surface 148 are substantially in contact. In other embodiments, the surfaces 124, 128 are substantially parallel but not perfectly parallel and thus are unable to maintain a perfectly flush contact surface. In some embodiments, when the pump side and patient side members 12, 14 are detachably coupled the securing arms 122 are slightly biased radially inward by the securing bar 146. This means that the securing arms 122 bias radially outward because the materials prefer to remain in an unbiased state. In other embodiments, the securing bar 146 is positioned in such a way that when the members 12, 14 are detachably coupled, the securing arms 122 and the securing bar 146 are in contact but the securing arms 122 are not biased radially inward.

FIGS. 17a-17f and 18a-18e demonstrate the process of detachment from and coupling of the pump side member 12 to the patient side member 14. In order for the pump side member 12 to detach from the patient side member 14, the securing arm 155 must pass or clear the securing bar 146.

Figure 18E:
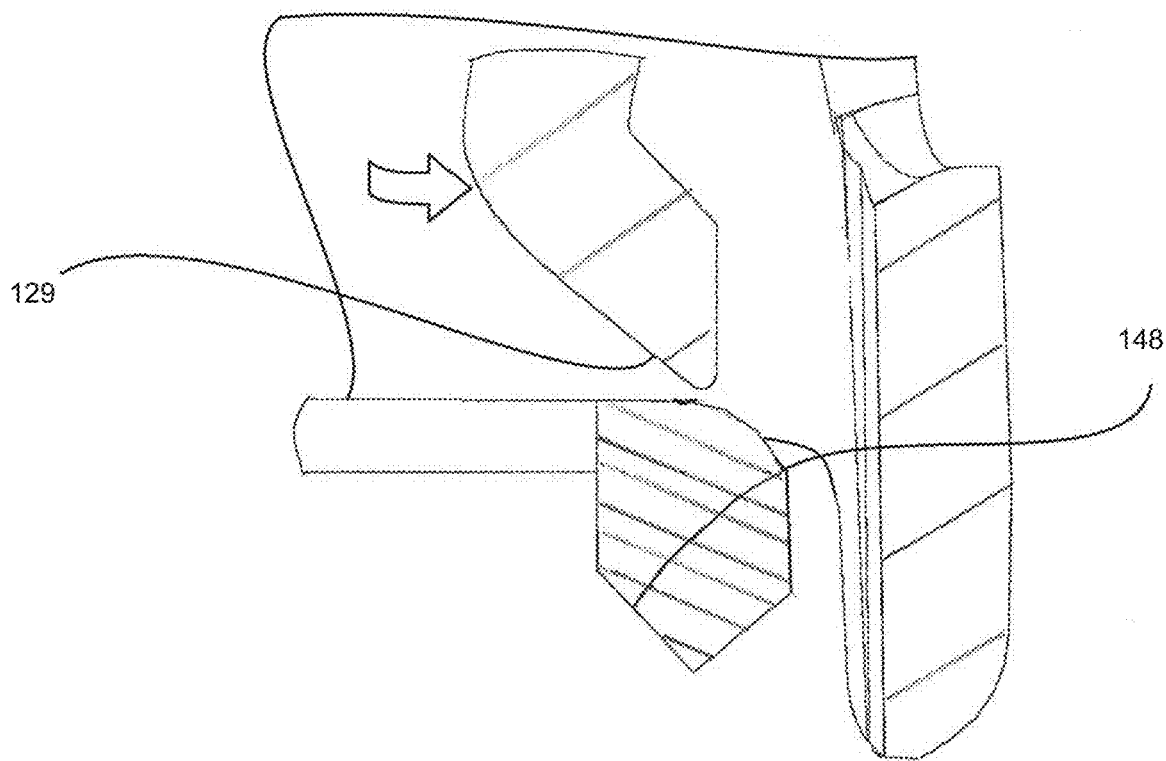
Figure 18E:
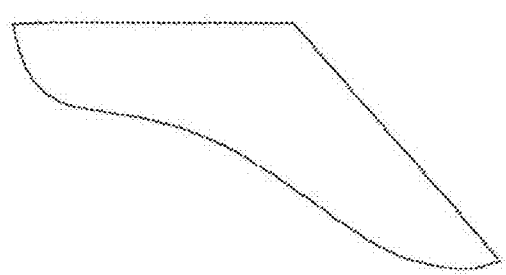

As previously mentioned, occasionally a patient or other circumstances may accidentally apply a force to IV tubing. This can result in the dislodgment of the delivery site 100 of the patient 102, potentially causing extensive damage to the tissues of the patient 102 as well as severe pain. The complementary nature of angled receiving surface 148 of the securing bar 146 and the gripping surface 124 of the securing arms 122 in some embodiments may provide for the detachability of the pump side member 12 from the patient side member 14. When an outwardly opposing axial force 170 is applied across the apparatus 10 (such as pulling IV tubing), because the angled receiving surface 148 and the gripping surface 124 are not parallel nor perpendicular to a radial axis 126, the angled receiving surface 148 exerts a force 172 perpendicular to the plane of the angled receiving surface 148 onto the gripping surface 124 in response to the outwardly opposing axial force 170 applied across the apparatus 10. This force 172 is transmitted to the securing arm 122. The securing arm 122 will subsequently bias radially inward from the force 172 exerted by the angled receiving surface 148 as a result of the outwardly opposing axial force 170 applied across the apparatus 10. See FIGS. 17b and 18b. When the securing arms 122 is biased radially inward, the materials of the securing arm 122 have some elasticity and exert a radially outward oriented force 174 in order to return the securing arm 122 to its resting position. After the members 12, 14 have detached, the securing arms 122 will snap back into an unbiased position as illustrated in FIG. 18e.

The outwardly opposing axial force 170 required to achieve detachment of the pump side and patient side members 12, 14 may be modified by varying several features of the apparatus 10. First, the angle 125, 149 at which the angled receiving surface 148 and the gripping surface 124 are disposed results in varying degrees of resistance to detachment. See FIG. 18d. For example, if the angled receiving surface 148 and the gripping surface 124 are set at an angle approaching 90 degrees relative to a radial axis 126, the resulting force 172 is more complementary to the direction of biasing of the securing arm 122 for detachment and will result in radially inward force applied to the securing arm 122 and will not result in axial force on the securing arm 122. Radially inward force will cause the securing arms 122 to bias radially inward. Axial force will result in tension on the securing arms 122, but will not bias the securing arms 122. The tension will instead provide resistance to the outwardly opposing axial forces 170. Thus, the closer to parallel the angled receiving surface 148 and the gripping surface 124 are relative to the radial axis 126, the more the force between the two components 124, 148 will be directed axially and not radially. Thus, greater outwardly opposing axial force 170 is required to result in a radially inward biasing of the securing arms 122. See FIG. 17e.

Second, the outwardly opposing axial force 170 required to achieve detachment may be varied by the length of the gripping surface 124. If the gripping surface 124 is longer, the securing arms 122 must bias a greater distance radially inward to clear the angled receiving surface 148 and the securing bar 146. A greater amount of force is required to bias the securing arm 122 radially inward, therefore, if a greater or lesser amount of outwardly opposing axial force 170 is desired for detachment, the length of the gripping surface 124 may be increased or decreased, respectively. This may cause certain material stress to the securing arm 122, thus the securing arm 122 may also comprise a reinforced joint 122a where the securing arm 122 extends from the anti-reconnection device 120.

Third, the texture of the angled receiving surface 148 and the gripping surface 124 may be altered to provide more resistance. As the outwardly opposing axial force 170 is applied to the apparatus 10, the gripping surface 124 is sliding relative to the angled receiving surface 148. The sliding motion creates an opposing frictional force. The greater the coefficient of friction is on the two surfaces 124, 148, the greater outwardly opposing axial force 170 required to detach the apparatus 10. The surface area of the two surfaces 124, 128 may be adjusted to provide varying levels of resistance. This includes larger or smaller surfaces 124, 148 or imperfect contact between the two surfaces 124, 148.

Fourth, the material and thickness of the securing arm 122 may also alter the amount of outwardly opposing axial force 170 necessary to detach the apparatus 10. When the securing arm 122 is comprised of thicker and more rigid material, a greater force is required to radially bias the securing arms 122. Thus, the force necessary to decouple the two members 12, 14 may be modified to maximize the effectiveness of the apparatus 10. For certain patients or insertion points, it may be necessary to have a low threshold tension or outwardly opposing axial force 170 to induce detachment as the tissue or the patient may be especially susceptible to damage or special sensitivities. Other situations may call for a higher threshold for decoupling. The toric joint 144 may also provide extra resistance to decoupling of the two members 12, 14.

The relationship between the securing arms 122 and the securing bar 146 in connection with the securing arm guards 136 provide the anti-reconnection feature of the present disclosure. The securing arms 122 further define a deflecting surface 129. When the pump side and patient side members 12, 14 are not coupled and the corresponding axes are aligned, the securing arm 122 and the securing bar 146 are aligned such that when the two members 12, 14 are translated across the axis 24 towards each other, the deflecting surface 129 of the securing arm 122 contacts the securing bar 146. The deflecting surface 129 obstructs further movement and the two members 12, 14 are not able to couple. In some embodiments, the deflecting surface 129 is angled substantially parallel to the gripping surface 124. The securing bar 146 may also be angled or rounded such that when a user applies inwardly opposing axial force 171 to the two members 12, 14 and the securing bar 146 is in contact with the deflecting surface 129, the securing arm 122 will radially bias outward, thus preventing the coupling of the two members 12, 14.

Because the deflecting surface 129 and the securing bar 146 are aligned to prevent coupling when the securing arm 122 is unbiased, in order to achieve coupling of the two members 12, 14, a user must manually bias the securing arms 122 radially inward such that the securing arm 122 clears and slides past the securing bar 146 when the two members 12, 14 are translated along the axis 24 towards the other. In some embodiments, the securing arm guards 136 prevent access to the securing arms 122. Access is only possible through the key hole 138. A special key is required to bias the securing arms 122 radially inward. This allows a medical care provider to limit the ability to couple the two members 12, 14 to those having access to a key. When unintentional de-couplings occur, a medical care provider may assess the situation and determine whether the line may be reconnected or if a new line needs to be used because of contamination or damage to the line.

One of skill in the art would readily recognize that the components previously described may be disposed on either of the members 12, 14 and may be relocated or reversed onto each of the members 12, 14. Thus, it is within the scope of this disclosure for the securing arms 122, securing arm guards 146, and any other part as recited in this disclosure located on the patient side member 14 to be relocated onto the pump side member 12 and for the securing bar 146 and other attendant elements located on the pump side member 12 to be relocated onto the patient side member 14. Furthermore, the valves 20, 22 and activating structures (cannula 32 and activating surface 32) may be resident on the opposite member 12, 14 as previously described when fluids are being extracted from a patient 102 rather than being administered to the patient 102.

In some embodiments, the two members 12, 14 may also comprise dead-end caps. The dead end caps are configured to prevent contamination of the inner channels and components of the members 12, 14. In some embodiments, the dead end caps may comprise the existing components such as the shield 127, securing bar 146, and securing arm guards 136. In other embodiments, the second end of the patient side members 110 is operable to act as a first dead end cap, and the proximate end of the pump side member 12 is operable to act as a second dead end cap. In other embodiments, a diameter of the channel 26 and the cannula 32 provide a protection against tampering with the valves 20, 22 of the apparatus 10. Patients, upon accidental disconnect, may try to reconnect the apparatus 10 and the diameter of the channel 26 and the cannula 32 prevent contact with the valves 20, 22 which could result in damage to the valves 20, 22 and loss of fluids due to damaged valves.

Because the apparatus 10 is being used in fluid transfer application, if a disconnect does occur, it is important that the flow of fluids through the device stop so as to prevent loss of fluids from a patient and prevent leakage of fluids from an IV bag, for instance. Some embodiments may implement a series of valves to prevent loss of fluids and resulting cleanup and danger from uncontained fluids. As previously discussed, a duckbill valve 22 may be implemented in the apparatus 10 to prevent the backflow of liquids in a direction opposite the desired flow. The duckbill valve 22 is positioned within the downstream portion of the two members 12, 14. Other unidirectional valves may also be implemented in various other embodiments, as well as multidirectional valves. Thus, if a patient is having fluids removed, the duckbill valve 22 would be in the pump side member 12 downstream from the patient 102, whereas the duckbill valve 22 would be proximate the patient 102 if fluids where being administered to the patient 102.

As previously discussed, a first valve 20 is needed to prevent fluids from continuing to flow from the source when the two members 12, 14 have detached. In some embodiments, this is accomplished by providing a first valve 20 that is only active when the two members 12, 14 are coupled together. This may be accomplished by providing a cannula 32 which extends into the pump side member 12 and activates a check valve or the first valve 20. The pressure provided by the valve activating surface 34 of the cannula 32 when the two members 12, 14 are coupled activates the first valve 20. When the two members 12, 14 are separated, the valve activating surface 34 is no longer applying pressure to the first valve 20, thus preventing fluids from flowing through the first valve 20. Some embodiments may utilize a commercially available check valve such as the QOSINA™ luer activated check valve.

In some embodiments, a toric joint 144 may be placed within the apparatus 10 to minimize fluid loss during decoupling. As the two members 12, 14 separate from one another, the valve activating surface 34 of the cannula 32 loses contact with the first valve 20. The toric joint 144 is disposed in the channel 26 such that the seal around the cannula 32 remains intact even after the first valve 20 is inactive. Thus, the system remains sealed for a period of time even after the first valve 20 is no longer active and fluids cannot pass into or through the apparatus 10. See FIGS. 17e and 17f.

Thus, although there have been described particular embodiments of the present invention of a new and useful BREAKAWAY MEDICAL TUBING CONNECTOR, it is not intended that such references be construed as limitations upon the scope of this invention.

What is claimed is:
1. A method of coupling a detachable line connector, comprising:
aligning a first channel of a first side member of the detachable line connector with a second channel of a second side member of the detachable line connector, wherein the first side member comprises a securing bar and wherein the second side member comprises a securing arm;

deflecting the securing arm of the second side member radially inward;

advancing the second side member and the first side member towards each other until the first channel and the second channel are in fluid communication;

releasing the securing arm, such that the securing arm of the second side member engages the securing bar of the first side member;

wherein the second side member further comprises a securing arm guard extending from the second side member and positioned radially outward from the securing arm, wherein the securing arm guard defines a key hole configured to permit access to the securing arm; and inserting a key into the key hole of the securing arm guard.

2. The method of claim 1, wherein the step of deflecting the securing arm is via the key.

3. The method of claim 2, further comprising activating a first valve of the first side member via a valve activating surface of the second side member, wherein first valve comprises a diaphragm, and wherein the valve activating surface of the second side member is axially spaced from the diaphragm while activating the first valve.

4. The method of claim 1, further comprising receiving a cannula of the second side member by a toric joint of the first side member.

5. The method of claim 1, further comprising sliding the securing arm past the securing bar when the securing arm is manually deflected radially inward.

6. The method of claim 1, wherein the securing arm and securing bar are positioned to resist coupling when the securing arm is in a neutral position.

\* \* \* \* \*